United States Patent
Goeke et al.

(10) Patent No.: US 9,656,938 B2
(45) Date of Patent: *May 23, 2017

(54) ORGANIC COMPOUNDS

(71) Applicant: Givaudan, S.A., Vernier (CH)

(72) Inventors: Andreas Goeke, Winterthur (CH); Philip Kraft, Dubendorf (CH); Heike Laue, Duebendorf (CH); Yue Zou, Shanghai (CN); Francis Voirol, Warth (CH)

(73) Assignee: Givaudan S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/888,887

(22) PCT Filed: May 8, 2014

(86) PCT No.: PCT/EP2014/059446
§ 371 (c)(1),
(2) Date: Nov. 3, 2015

(87) PCT Pub. No.: WO2014/180952
PCT Pub. Date: Nov. 13, 2014

(65) Prior Publication Data
US 2016/0075627 A1   Mar. 17, 2016

(30) Foreign Application Priority Data

May 8, 2013 (GB) .................................. 1308236.7

(51) Int. Cl.
| | | |
|---|---|---|
| C07C 47/00 | (2006.01) |
| A61K 8/00 | (2006.01) |
| C07C 47/347 | (2006.01) |
| C07C 47/228 | (2006.01) |
| C07C 47/453 | (2006.01) |
| C11B 9/00 | (2006.01) |
| A61K 8/33 | (2006.01) |
| A61Q 13/00 | (2006.01) |
| C07C 47/11 | (2006.01) |

(52) U.S. Cl.
CPC .............. *C07C 47/347* (2013.01); *A61K 8/33* (2013.01); *A61Q 13/00* (2013.01); *C07C 47/11* (2013.01); *C07C 47/228* (2013.01); *C07C 47/453* (2013.01); *C11B 9/0061* (2013.01); *C07C 2102/08* (2013.01)

(58) Field of Classification Search
CPC ... C07C 47/228; C07C 47/347; C07C 47/453; C11B 9/0061; A61K 8/33
USPC .................... 568/425, 440; 435/188; 512/21
See application file for complete search history.

(56) References Cited

U.S. PATENT DOCUMENTS

| | | |
|---|---|---|
| 3,548,006 A | 12/1970 | Scriabine |
| 5,095,152 A | 3/1992 | Frank |
| 5,527,769 A | 6/1996 | Winter et al. |
| 6,103,688 A | 8/2000 | Winter et al. |
| 6,342,612 B1 | 1/2002 | Sprecker et al. |
| 6,465,410 B1 | 10/2002 | Bettiol et al. |
| 8,754,028 B2 | 6/2014 | Velazquez et al. |
| 2008/0146636 A1 | 6/2008 | Erickson et al. |
| 2009/0099228 A1 | 4/2009 | Aissaoui et al. |
| 2010/0152083 A1 | 6/2010 | Velazquez et al. |
| 2011/0021589 A1 | 1/2011 | Vacher et al. |
| 2014/0234244 A1 | 8/2014 | Zenhausern |
| 2014/0296225 A1 | 10/2014 | Tang et al. |
| 2016/0108342 A1 | 4/2016 | Goeke et al. |

FOREIGN PATENT DOCUMENTS

| | | |
|---|---|---|
| FR | 1.460.826 A | 1/1966 |
| FR | 1.430.164 A | 3/1966 |
| GB | 988502 | 4/1965 |
| GB | 1057360 | 2/1967 |
| JP | H 3-221599 A | 9/1991 |
| WO | WO 94/27946 A1 | 12/1994 |
| WO | WO 2008/065021 A1 | 6/2008 |
| WO | WO 2009/027957 A2 | 3/2009 |
| WO | WO 2010/105873 A2 | 9/2010 |
| WO | WO 2012/172122 A2 | 12/2012 |
| WO | WO 2013/045301 A1 | 4/2013 |
| WO | WO 2013/062892 A1 | 5/2013 |

OTHER PUBLICATIONS

PCT/EP2014/059446—International Search Report, mailed Oct. 13, 2014.
PCT/EP2014/059446—International Written Opinion, mailed Oct. 13, 2014.
PCT/EP2014/059446—International Preliminary Report on Patentability, issued Nov. 10, 2015.
GB 13082363.7—British Search Report, Nov. 4, 2013.
CH 00577/14—Swiss Search Report, May 15, 2014.
Aronica, et al., "Silylation-Desilylation of Propargyl Amides: Rapid Synthesis of Functionalised Aldehydes and β-Lactams", Tetrahedron, Apr. 25, 2007, pp. 6843-6854. vol. 63, No. 29, Elsevier Science Publishers, Amsterdam, NL.
Cagen, et al. "Toxicity Induced by Subchronic Dermal Exposure to Paratertiary Butyl Benzoic Acid (pt BBA) in Fischer 344 Rats", International Journal of Toxicology, Sep./Oct. 1989, pp. 1027-1038, vol. 8, No. 5.
Cheng, et al., "Arylation of Aldehyde Homoenolates With Aryl Bromides", Organic Letters, Apr. 24, 2013, pp. 2298-2301, vol. 15, No. 9.
Hunter, et al., "Studies on the Oral Toxicity of p-tert-Butyl Benzoic Acid in Rats", Food and Cosmetics Toxicology, 1965, pp. 289-298, vol. 3. (Abstract only).

(Continued)

*Primary Examiner* — Sikarl Witherspoon
(74) *Attorney, Agent, or Firm* — Curatolo Sidoti Co., LPA; Joseph G. Curatolo; Salvatore A. Sidoti

(57) ABSTRACT

An aryl-substituted alkanal compound having a molecular weight of less than 300 g/mol and which bears a substituent on the aryl ring ortho to a substituent bearing the aldehyde functionality. Said compounds are useful as perfume ingredients in personal care and household care products.

16 Claims, No Drawings

(56) References Cited

OTHER PUBLICATIONS

Kologrivova, et al., "Isomeric Composition of Aliphatic-Aromatic Aldehydes Obtained From Unsaturated Aldehydes and Aromatic Hydrocarbons", Trudy/Vsesojuznyj Naucno-Issledovatel'Skij Institut Sinteticeskich I Natural'Nych Dusistych Vescestv, Ministerstvo Promyslennosti Prodovol'Stvennych Tovarov, MPPT, SSSR, Piscepromoizdat, USSR, Jan. 1, 1971, pp. 96-101, vol. 9.
Lamboley, et al., "Synthesis and Properties of Conformationally Constrained Analogues of Floral-Type Oderants", Helvetica Chimica ACTA, Jul. 1, 2004, pp. 1767-1793, vol. 87, No. 7.
McCune, et al., "Inhibition of Hepatic Gluconeogenesis and Lipogenesis by Benzoic Acid, p-tert.-Butylbenzoic Acid, and A Structurally Related Hypolipidemic Agent Sc-33459", Archives of Biochemistry and Biophysics, pp. 124-133, Mar. 1982, vol. 214, Issue 1. (Abstract only).
Skouroumounis, et al., "Synthesis of 1,3,4,5-Tetrahydro-2-Benzoxepin Derivatives as Conformationally Restricted Analogues of Cyclamenaldehyde-Type Compounds and as Intermediates for Highly Odour-Active Homologues", Helvetica Chimica ACTA, Jan. 1, 1996, pp. 1095-1109, vol. 79, No. 4.
Winter, et al., "Synthesis and Odor Properties of Substituted Indane-2-Carboxaldehydes, Discovery of a New Floral (Muguet) Fragrance Alcohol", Helvetica Chimica ACTA, Dec. 1, 2005, pp. 3118-3127, vol. 88. No. 12.
Office Action mailed Oct. 11, 2016, for Chinese patent application No. 201480025639.3.
201480025639.3—Chinese Search Report, mailed Oct. 11, 2016.
GB1308248.2—Great Britain Search Report, mailed Oct. 23, 2013.
Office Action mailed Oct. 11, 2016, for U.S. Appl. No. 14/888,633.
PCT/EP2014/059427—International Preliminary Report on Patentability, issued Nov. 11, 2015.

ORGANIC COMPOUNDS

CROSS REFERENCE TO RELATED APPLICATIONS

This application is a national stage application of International Application No. PCT/EP2014/059446, filed 8 May 2014, which claims priority from Great Britain Patent Application No. 1308236.7, filed 8 May 2013, from which applications priority is claimed, and which are incorporated herein by reference.

This invention relates to perfume ingredients and perfume preparations containing same. In particular, the invention relates to said perfume ingredients or perfume preparations that exhibit muguet (lily of the valley) odour characteristics. Still more particularly, the invention relates to said perfume preparations that contain no, or substantially no, Lilial™. The invention further relates to methods of making said perfume ingredients and perfume preparations, as well as the use of said perfume ingredients and perfume preparations in fine fragrances and consumer products, such as personal care and household care products. The invention also relates to said fine fragrances and consumer products containing said perfume ingredients or perfume preparations.

Compounds having muguet odour characteristics are very sought after perfume ingredients. These compounds are important ingredients in floral bases and can act as harmonizers across many different types of fragrance creations. Compounds of this type are used widely in consumer products, such as personal care and consumer care products, as well as in fine perfumery, to generate pleasant odours or to mask unpleasant odours.

An excellent perfume ingredient widely valued for its muguet odour note is Lilial™. Lilial™ is an example of an aryl-substituted alkanal, more particularly an aryl-substituted propanal. Specifically, its chemical name is 3-(4-tert-butylphenyl)-2-methylpropanal (CAS 80-54-6). This compound has found wide use in fine perfumery as well as in personal and household care products. However, its use has come under regulatory scrutiny in view of recent findings that it exhibits toxic effects on the reproductive organs of male rats and dogs. No effects were found in studies with mice, guinea-pigs and primates, nevertheless, under the Global Harmonized System (GHS) classification system this compound is classified as a CMR2 material. For CMR category 2 materials, it is necessary to establish that quantities proposed for use are harmless to consumers. In view of the regulatory situation of Lilial™ there is a need to replace it with other perfume ingredients.

WO2010105 873 addresses the problem of replacing Lilial™. The proposed solution resides in the use of mixtures of known ingredients commonly found in the perfumery palette in order to recreate odour characteristics substantially similar to those of Lilial™.

Likewise, WO2009027957 proposes a solution residing in the formulation of combinations of known perfume ingredients from the perfumery palette.

WO2013045301 also propose a solution to Lilial™ replacement, which resides in the selection of mixtures of ingredients including the compound Lilyflore™ and a certain indanyl propanal compound, in combination with other secondary perfuming ingredients.

The applicant has now found compounds that can be employed as perfume ingredients in perfume compositions and consumer products. More particularly, the applicant has found compounds that possess desirable muguet odour characteristics. Still more particularly, the applicant has found compounds that possess odour characteristics, which may be perceived and recognised by perfumers as being very reminiscent of the odour of Lilial™ and so can serve as a simple replacement for Lilial™. Furthermore, the compounds may have similar or even improved perfume performance compared with Lilial™. Finally, the applicant has found compounds that do not attract the regulatory concerns associated with Lilial™. In particular, the applicant has found that aryl-substituted alkanal perfume ingredients that are close structural analogues to Lilial™ but which, critically, contain a substituent on the aryl ring, which is positioned ortho to the group bearing the aldehyde functionality, have similar odour characteristics as Lilial™, but surprisingly carry with them none of the CMR-related issues associated with Lilial™ as indicated by in vitro data.

Accordingly, the invention provides in a first aspect an aryl-substituted alkanal compound having a molecular weight of less than 300 g/mol and which bears a substituent on the aryl ring ortho to a substituent bearing the aldehyde functionality, wherein said compound is not 5-(tert-butyl)-2-methyl-2,3-dihydro-1H-indene-2-carbaldehyde, 5-(tert-butyl)-2,3-dihydro-1H-indene-2-carbaldehyde, 5-isopropyl-2,3-dihydro-1H-indene-2-carbaldehyde, 5-isopropyl-2-methyl-2,3-dihydro-1H-indene-2-carbaldehyde, 5-ethyl-2,3-dihydro-1H-indene-2-carbaldehyde, 5-ethyl-2-methyl-2,3-dihydro-1H-indene-2-carbaldehyde, 5-methyl-2,3-dihydro-1H-indene-2-carbaldehyde, 2,5-dimethyl-2,3-dihydro-1H-indene-2-carbaldehyde, 3-(5-(tert-butyl)-2-methylphenyl)propanal, 3-(5-(tert-butyl)-2-methylphenyl)-2-methylpropanal, 3-(5-isopropyl-2-methylphenyl)propanal, 3-(5-isopropyl-2-methylphenyl)-2-methylpropanal, 3-(5-ethyl-2-methyl phenyl)propanal, 3-(5-ethyl-2-methylphenyl)-2-methylpropanal, 3-(4-(tert-butyl)-2-methylphenyl)propanal, 3-(4-(tert-butyl)-2-methylphenyl)-2-methylpropanal, 3-(4-isopropyl-2-methylphenyl)propanal, 3-(4-isopropyl-2-methylphenyl)-2-methylpropanal, 3-(4-ethyl-2-methylphenyl)propanal, 3-(4-ethyl-2-methylphenyl)-2-methylpropanal or any of the compounds of formula 3 set forth hereinbelow in which each of $R_1$ through $R_5$ is H or methyl.

In a particular embodiment compounds of the present invention are represented by the formula

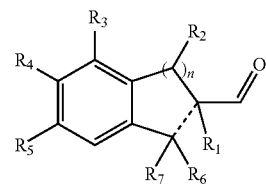

Formula 1 wherein
$R_1$, $R_2$, $R_3$, $R_6$ and $R_7$ each independently may represent H or methyl;
$R_4$ is H, or when $R_5$ is H, $R_4$ is a $C_1$-$C_7$ branched or linear, saturated or unsaturated unsubstituted or substituted, optionally with cyclopropyl groups, alkyl residue;
$R_5$ is H, or when $R_4$ is H, $R_5$ is a $C_1$-$C_7$ branched or linear, saturated or unsaturated, unsubstituted or substituted, optionally with cyclopropyl groups, alkyl residue; or
$R_4$ and $R_5$ together with the carbon atoms to which they are attached, form a substituted or unsubstituted 5-membered ring;

n=0, 1, 2;

the dotted line represents an optional single bond, with the proviso that when the dotted line represents a single bond $R_4$ or $R_5$ are sec-butyl, iso-butyl or a $C_5$-$C_7$ branched or linear, saturated or unsaturated alkyl residue; and wherein the compounds are not selected from 5-(tert-butyl)-2-methyl-2,3-dihydro-1H-indene-2-carbaldehyde, 5-(tert-butyl)-2,3-dihydro-1H-indene-2-carbaldehyde, 5-isopropyl-2,3-dihydro-1H-indene-2-carbaldehyde, 5-isopropyl-2-methyl-2,3-dihydro-1H-indene-2-carbaldehyde, 5-ethyl-2,3-dihydro-1H-indene-2-carbaldehyde, 5-ethyl-2-methyl-2,3-dihydro-1H-indene-2-carbaldehyde, 5-methyl-2,3-dihydro-1H-indene-2-carbaldehyde, 2,5-dimethyl-2,3-dihydro-1H-indene-2-carbaldehyde, 3-(5-(tert-butyl)-2-methylphenyl)propanal, 3-(5-(tert-butyl)-2-methylphenyl)-2-methylpropanal, 3-(5-isopropyl-2-methylphenyl)propanal, 3-(5-isopropyl-2-methylphenyl)-2-methylpropanal, 3-(5-ethyl-2-methylphenyl)propanal, 3-(5-ethyl-2-methylphenyl)-2-methylpropanal, 3-(4-(tert-butyl)-2-methylphenyl)propanal, 3-(4-(tert-butyl)-2-methylphenyl)-2-methylpropanal, 3-(4-isopropyl-2-methylphenyl)propanal, 3-(4-isopropyl-2-methylphenyl)-2-methylpropanal, 3-(4-ethyl-2-methylphenyl)propanal, 3-(4-ethyl-2-methylphenyl)-2-methylpropanal or any of the compounds of formula 3 set forth hereinbelow in which each of $R_1$ through $R_5$ is H or methyl.

In another particular embodiment compounds of the present invention are represented by the formula

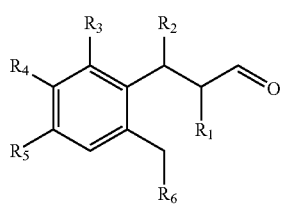

Formula 2 wherein $R_1$, $R_2$, $R_3$, and $R_6$ each independently may represent H or methyl;

$R_4$ is H, or when $R_5$ is H, $R_4$ is a $C_1$-$C_7$ branched or linear, saturated or unsaturated unsubstituted or substituted, optionally with cyclopropyl groups, alkyl residue;

$R_5$ is H, or when $R_4$ is H, $R_5$ is a $C_1$-$C_7$ branched or linear, saturated or unsaturated, unsubstituted or substituted, optionally with cyclopropyl groups, alkyl residue; or $R_4$ and $R_5$ together with the carbon atoms to which they are attached, form a substituted or unsubstituted 5-membered ring; and wherein the compounds are not 3-(5-(tert-butyl)-2-methylphenyl)propanal, 3-(5-(tert-butyl)-2-methylphenyl)-2-methylpropanal, 3-(5-isopropyl-2-methylphenyl) propanal, 3-(5-isopropyl-2-methylphenyl)-2-methylpropanal, 3-(5-ethyl-2-methyl phenyl)propanal, 3-(5-ethyl-2-methylphenyl)-2-methylpropanal, 3-(4-(tert-butyl)-2-methylphenyl)propanal, 3-(4-(tert-butyl)-2-methylphenyl)-2-methylpropanal, 3-(4-isopropyl-2-methylphenyl)propanal, 3-(4-isopropyl-2-methylphenyl)-2-methylpropanal, 3-(4-ethyl-2-methylphenyl)propanal, 3-(4-ethyl-2-methylphenyl)-2-methylpropanal or any of the compounds of formula 3 set forth hereinbelow in which each of $R_1$ through $R_5$ is H or methyl.

In yet another embodiment of the present invention there is provided a compound according to the formula

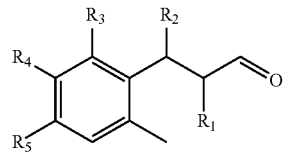

Formula 3 wherein $R_1$, $R_2$, and $R_3$ each independently may represent H or methyl;

$R_4$ is H, or when $R_5$ is H, $R_4$ is an iso-butyl, sec-butyl or linear, saturated or unsaturated, unsubstituted or substituted (optionally with cyclopropyl groups) $C_5$-$C_7$ alkyl or alkenyl residue; and $R_5$ is H, or when $R_4$ is H, $R_5$ is an iso-butyl, sec-butyl or linear, saturated or unsaturated, unsubstituted or substituted (optionally with cyclopropyl groups) $C_5$-$C_7$ alkyl or alkenyl residue; and wherein the compounds are not 3-(5-(tert-butyl)-2-methylphenyl)propanal, 3-(5-(tert-butyl)-2-methylphenyl)-2-methylpropanal, 3-(5-isopropyl-2-methylphenyl)propanal, 3-(5-isopropyl-2-methylphenyl)-2-methylpropanal, 3-(5-ethyl-2-methylphenyl) propanal, 3-(5-ethyl-2-methylphenyl)-2-methylpropanal, 3-(4-(tert-butyl)-2-methylphenyl)propanal, 3-(4-(tert-butyl)-2-methylphenyl)-2-methylpropanal, 3-(4-isopropyl-2-methylphenyl)propanal, 3-(4-isopropyl-2-methylphenyl)-2-methylpropanal, 3-(4-ethyl-2-methylphenyl) propanal, 3-(4-ethyl-2-methylphenyl)-2-methylpropanal or any of the compounds of formula 3 set forth hereinbelow in which each of $R_1$ through $R_5$ is H or methyl.

In yet another particular aspect of the present invention there is provided a compound of the formula

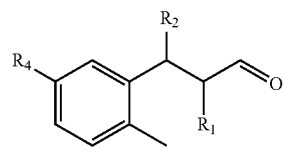

Formula 4 wherein $R_1$ and $R_2$, each independently may represent H or methyl; and $R_4$ represents an iso-butyl or sec-butyl group, or a saturated or unsaturated $C_5$-$C_7$ alkyl or alkenyl residue, which may be unsubstituted or substituted, optionally with cyclopropyl groups.

In yet another particular embodiment of the present invention there is provided a compound of the formula

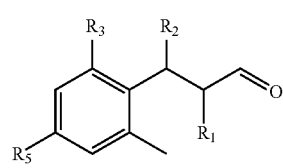

Formula 5 wherein $R_1$, $R_2$, and $R_3$ each independently may represent H or methyl; and R₅ is a an iso-butyl or sec-butyl group, or a saturated or unsaturated C₅-C₇ alkyl or alkenyl residue, which may be unsubstituted or substituted, optionally with cyclopropyl groups.

In yet another aspect of the present invention there is provided a compound of the formula

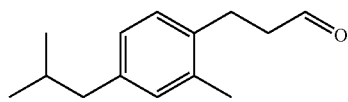

Particularly compounds of the present invention include 3-(4-isobutyl-2-methylphenyl)propanal, 3-(4-isobutyl-2,6-dimethylphenyl)propanal, 3-(4-isobutyl-2-methylphenyl)-2-methylpropanal, 3-(4-isobutyl-2-methylphenyl)butanal, 3-(4-(sec-butyl)-2-methylphenyl)propanal, 3-(2-methyl-4-(tert-pentyl)phenyl)propanal, 3-(4-isopentyl-2-methylphenyl)propanal, 3-(2-methyl-4-(4-methylpentyl)phenyl)propanal, 3-(2-methyl-5-(4-methylpentyl)phenyl)propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl)phenyl)propanal, 3-(5-isobutyl-2-methylphenyl)propanal, 3-(2-methyl-4-(2-methylbutyl)phenyl)propanal, 5-isobutyl-2,3-dihydro-1H-indene-2-carbaldehyde, 3-(1,1,6-trimethyl-2,3-dihydro-1H-inden-5-yl)propanal, 3-(2-methyl-5-(4-methylpentyl)phenyl)propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl)phenyl)propanal, 3-(5-Isobutyl-2-methylphenyl)propanal, 3-(4-Isobutyl-2-methylphenyl)propanal, 3-(4-isobutyl-2,6-dimethylphenyl)propanal, 3-(4-isobutyl-2-methylphenyl)-2-methylpropanal, 3-(4-isobutyl-2-methylphenyl)butanal, 3-(4-(sec-butyl)-2-methylphenyl)propanal, 3-(2-methyl-4-(tert-pentyl)phenyl)propanal, 3-(4-isopentyl-2-methylphenyl)propanal and 3-(2-methyl-4-(4-methylpentyl)phenyl)propanal.

The compounds of the present invention possess substantially similar odour characteristics and performance characteristics as Lilial™. As such, and in contradistinction to the prior art proposals related to Lilial™ replacement based on mixtures of known ingredients, the present invention can achieve Lilial™ replacement based on a single compound. This has the obvious advantage of representing a cost-effective solution to the replacement problem, but it is also makes the perfumers' creative process simpler.

Furthermore, compounds of the present invention can generate particularly substantive and long-lasting muguet odour characteristics.

The compounds of the present invention are particularly impactful perfume ingredients. The impact that a perfume ingredient exerts is related to its Odour Value. Odour Value is the ratio of vapour pressure to detection threshold concentration.

The compounds have extremely high Odour Values. For example, the compound

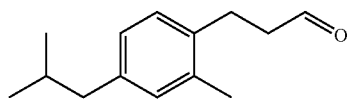

has an Odour Value of 559'071. Related perfume ingredients are not impactful by comparison. For example Lilial™ has an odour value of only 32'978 whereas cyclamen aldehyde has an Odour Value of only 21'986.

The remarkably high Odour Value of the compounds of the present invention is significant in that there is a need for sustainability and the provision of impactful perfume ingredients enables perfumers to create desirable fragrance accords with lower concentrations of materials.

The regulatory issues surrounding Lilial™ are born from the fact that it is enzymatically degraded in rats and dogs to tert-butyl benzoic acid (t-BBA), which is known to inhibit glucose synthesis and fatty acid synthesis in vitro (McCune et al, Arch Biochem Biophys (1982) 214 (1): 124-133).

tert-Butyl benzoic acid is known to cause testicular effects in male rats (Hunter et al. Food Cosmet. Toxicol. 1965, 3: 289-298; Cagen et al. J. Am. Coll. Toxicol. 1989, 8 (5): 1027-1038).

In contrast, the compounds of the present invention are not susceptible to enzyme-mediated degradation to corresponding benzoic acid derivatives in vitro. This was indeed a very surprising result considering their close structural similarity to Lilial™.

The applicant's surprising discovery that aryl-substituted alkanal perfume ingredients substituted on the ring at a position ortho to the group bearing the aldehyde functionality are not converted to their corresponding benzoic acid derivatives, provides an insight not heretofore appreciated in the art, which enables perfumers to employ a class of compounds that although being structurally similar to Lilial™ (and therefore possessing remarkably similar olfactive properties as these compounds), nevertheless do not raise regulatory issues.

In order to study in vitro metabolism in rat hepatocytes, Lilial™ and compounds of the present invention may be incubated in the presence of rat hepatocytes in suspension. Reduction in the concentration of Lilial™ and the compounds of the present invention and formation of any of the corresponding benzoic acid derivatives may be analysed by GC-MS.

In another aspect of the present invention there is provided a compound as herein above defined, which after incubation with hepatocytes isolated from rats, is substantially free of its corresponding benzoic acid degradation product. By "substantially free" is meant that if it is present it is below levels of detection, e.g. less than 1%, more particularly less than 1% to 0%. As such, compounds of the present invention provide perfumers with an eminently suitable surrogate for the valuable yet problematic Lilial™.

Accordingly, the invention provides in another of its aspects the use of a compound defined hereinabove as a perfume ingredient.

The invention provides in another of its aspects the use of a compound defined hereinabove in a perfume composition as a replacement for aryl-substituted alkanal odourants, more particularly aryl-substituted propanal odourants, which are unsubstituted on the aryl ring at a position ortho to the substituent bearing the aldehyde functionality, in particular Lilial™.

In another aspect of the invention there is provide a method of imparting a muguet odour characteristic to a perfume composition, said method comprising the step of incorporating a compound defined hereinabove into said perfume composition.

In yet another aspect of the invention there is provided a perfume composition comprising a compound defined hereinabove.

In yet another aspect of the invention there is provided a perfume composition possessing muguet odour characteristics comprising a compound defined hereinabove.

In yet another aspect of the present invention there is provided a perfume composition comprising a compound defined hereinabove that is free of any aryl-substituted alkanal odourants, more particularly aryl-substituted propanal odourants, which are unsubstituted on the aryl ring at a position ortho to the substituent bearing the aldehyde functionality, in particular Lilial™.

A perfume composition according to the present invention can be made up entirely by one or more of the compounds of the present invention. However, a perfume composition may also contain, in addition to one or more of the compounds of present invention, one or more additional perfume ingredients.

Compounds of the present invention may be present in a perfume composition in any amount depending on the particular olfactive effect that a perfumer wishes to achieve. In a particular embodiment of the present invention, a perfume composition of the present invention may contain compounds defined hereinabove in an amount of 0.1 to 100% by weight of said composition.

If one or more additional perfume ingredients are employed, they may be selected from perfume ingredients known in the art.

In particular, said perfume ingredients that may be employed in a perfume composition according to the invention include 6-methoxy-2,6-dimethylheptan-1-al (methoxymelonal), 5,9-dimethyl-4,8-decadienal (geraldehyde), beta-methyl-3-(1-methylethyl)benzenepropanal (Florhydral), octahydro-8,8-dimethylnaphthalene-2-carbaldehyde (Cyclomyral), alpha-methyl-1,3-benzodioxole-5-propionaldehyde (helional), 5-methyl-2-(1-methylbutyl)-5-propyl-1,3-dioxan (Troenan), 3-(o-ethylphenyl)-2,2-di methyl propionaldehyde (Floralozone), farnesol, 3,7,11-trimethyldodeca-1,6,10-trien-3-ol, optionally as an isomeric mixture (nerolidol), 2-methyl-4-phenylbutan-2-ol (dimethylphenylethylcarbinol), cis-4-(isopropyl)cyclohexanemethanol (Mayol), 1-(1-hydroxyethyl)-4-(1-methylethyl)cyclohexane (optionally as a mixture of the diastereoisomers) (mugetanol), (4-methyl-3-pentenyl)cyclohexenecarbaldehyde (Citrusal), cyclohexyl salicylate, hexyl salicylate, benzyl salicylate, amyl salicylate, 3-(p-(2-methylpropyl)phenyl)-2-methyl propionaldehyde (Silvial), 3-p-cumenyl-2-methylpropionaldehyde (cyclamenaldehyde), mixtures of: cis-tetrahydro-2-isobutyl-4-methylpyran-4-ol; trans-tetrahydro-2-isobutyl-4-methylpyran-4-ol; (Florol), triethyl citrate and dipropylene glycol.

Said perfume ingredients may additionally include Amyl Salicylate (2050-08-0); Aurantiol® (89-43-0); Benzyl Salicylate (118-58-1); Cis-3-hexenyl Salicylate (65405-77-8); Citronellyl Oxyacetaldehyde (7492-67-3); Cyclemax (7775-00-0); Cyclohexyl Salicylate (25485-88-5); Cyclomyral® (68738-94-3); Citronellol (106-22-9); Geraniol (106-24-1); Cyclopentol Hc 937165 (84560-00-9); Cymal (103-95-7); Dupical (30168-23-1); Ethyl Linalool (10339-55-6); Floral Super (71077-31-1); Florhydral® (125109-85-5); Florol® (63500-71-0); Gyrane (24237-00-1); Hexyl Salicylate (6259-76-3); Helional™ (1205-17-0); Hydroxycitronellal (107-75-5); Linalool (78-70-6); Lyral® (31906-04-4); Majantol® (103694-68-4); Mayol® (13828-37-0); Melafleur (68991-97-9); Melonal (106-72-9); Mugetanol (63767-86-2); Muguesia (56836-93-2); Muguet alcohol (13351-61-6); Verdantiol (91-51-0); Peonile® (10461-98-0); Phenoxanol® (55066-48-3); Rossitol® (215231-33-7); Silvial® (6658-48-6); Suzural (6658-48-6); Muguol® (18479-57-7); Tetrahydro Linalol (78-69-3); Acalea (84697-09-6); Dihydro Iso Jasmonate (37172-53-5); Hexyl Cinnamic Aldehyde (101-86-0); Hedione® (24851-98-7); Acetoin (513-86-0); Adoxal (141-13-9); Aldolone® (207228-93-1); Ambrocenide® (211299-54-6); Ambroxan (3738-00-9); Azurone® (362467-67-2); Bacdanol® (28219-61-6); Calone 1951 ® (28940-11-6); Cetalox® (3738-00-9); Cinnamic alcohol (104-54-1); Citral (5392-40-5); Cyclabute (67634-20-2); Cyclacet™ (5413-60-5); Cyclaprop™ (17511-60-3); Cyclohexadecanolide (109-29-5); Cyclohexadecenone (3100-36-5); Cyclopentadecanone (507-72-7); Delta Damascone (57378-68-4); Ebanol® (67801-20-1); Elintaal Forte (40910-49-4); Ethyl Vanillin (121-32-4); Ethylene Brassylate (105-95-3); Exaltenone 942008 (14595-54-1); Exaltolide Total 935985 (106-02-5); Floralozone (67634-14-4); Fructalate (72903-27-6); Gamma Decalactone (706-14-9); Habanolide (111879-80-2); Helvetolide® (141773-73-1); Hexamethylindanopyran (1222-05-5); Hydroxyambran® (118562-73-5); Iso E Super® (54464-57-2); Iso Hexenyl Cyclohexenyl Carboxaldehyde (37677-14-8); Jasmal (18871-14-2); Javanol® (198404-98-7); Lauric Aldehyde (112-54-9); Mefranal (55066-49-4); Muscenone (63314-79-4); Tonalid® (1506-02-1); Nectaryl® (95962-14-4); Norlim Banol (70788-30-6); Para Hydroxy Phenyl Butanone (5471-51-2); Pino Acetaldehyde (33885-51-7); Romandolide® (236391-76-7); Sanjinol (28219-61-6); Silvanone® Supra (109-29-5/507-72-7); Terpineol (8000-41-7); Vanillin (121-33-5); and Velvione® (37609-25-9), wherein, the figures in parentheses are CAS numbers.

A perfume composition need not be limited to the perfume ingredients listed above. Other perfume ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like.

The perfume ingredients contained in said perfume composition are described above, but of course, the perfume composition may not be limited to the stated ingredients. In particular, perfume mixtures may comprise adjuvants that are commonly employed in perfume formulations. The term "adjuvants" refers to an ingredient that might be employed in a perfume composition for reasons other than, or not specifically, related to the composition's olfactive performance. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or composition containing same. A detailed description of the nature and type of adjuvants commonly used in perfume mixture or compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

Furthermore, any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume, which will react in a suitable environment to release the perfume ingredient in a controlled manner.

Having regard to the foregoing, it will be appreciated that a perfume composition may be at least partly in solid form, in gel form, in foam form and/or liquid form. If it is present in solid form, it then it may take the form of granules, powders or tablets.

The present invention provides in another of its aspects a fine fragrance or consumer product, such as a personal care or household care composition that is perfumed by an aryl-substituted alkanal compound having a molecular weight of less than 300 g/mol and which bears a substituent on the aryl ring ortho to a substituent bearing the aldehyde functionality.

In a particular embodiment the invention provides a fine fragrance or consumer product such as a personal care or household care composition that is perfumed by a compound represented by the formula

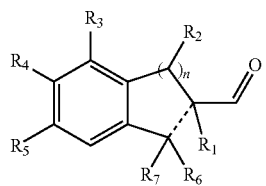

Formula 1 wherein, $R_1$, $R_2$, $R_3$, $R_6$ and $R_7$ each independently may represent H or methyl;
$R_4$ is H, or when $R_5$ is H, $R_4$ is a $C_1$-$C_7$ branched or linear, saturated or unsaturated unsubstituted or substituted, optionally with cyclopropyl groups, alkyl residue;
$R_5$ is H, or when $R_4$ is H, $R_5$ is a $C_1$-$C_7$ branched or linear, saturated or unsaturated, unsubstituted or substituted, optionally with cyclopropyl groups, alkyl residue; or
$R_4$ and $R_5$ together with the carbon atoms to which they are attached, form a substituted or unsubstituted 5-membered ring;
n=0, 1, 2;
the dotted line represents an optional single bond, with the proviso that when the dotted line represents a single bond $R_4$ or $R_5$ are sec-butyl, iso-butyl or a $C_5$-$C_7$ branched or linear, saturated or unsaturated alkyl residue.

In another particular embodiment the invention provides a fine fragrance or consumer product, such as a personal care or household care composition that is perfumed by a compound represented by the formula

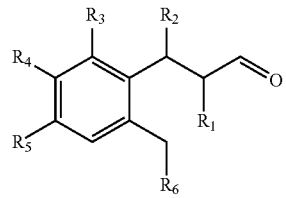

Formula 2 wherein
$R_1$, $R_2$, $R_3$, and $R_6$ each independently may represent H or methyl;
$R_4$ is H, or when $R_5$ is H, $R_4$ is a $C_1$-$C_7$ branched or linear, saturated or unsaturated unsubstituted or substituted, optionally with cyclopropyl groups, alkyl residue;
$R_5$ is H, or when $R_4$ is H, $R_5$ is a $C_1$-$C_7$ branched or linear, saturated or unsaturated, unsubstituted or substituted, optionally with cyclopropyl groups, alkyl residue; or
$R_4$ and $R_5$ together with the carbon atoms to which they are attached, form a substituted or unsubstituted 5-membered ring.

In another particular embodiment the invention provides a fine fragrance or consumer product, such as a personal care or household care composition that is perfumed by a compound represented by the formula

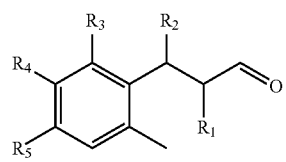

Formula 3 wherein
$R_1$, $R_2$, and $R_3$ each independently may represent H or methyl;
$R_4$ is H, or when $R_5$ is H, $R_4$ is an iso-butyl, sec-butyl or linear, saturated or unsaturated, unsubstituted or substituted (optionally with cyclopropyl groups) $C_5$-$C_7$ alkyl or alkenyl residue; and
$R_5$ is H, or when $R_4$ is H, $R_5$ is an iso-butyl, sec-butyl or linear, saturated or unsaturated, unsubstituted or substituted (optionally with cyclopropyl groups) $C_5$-$C_7$ alkyl or alkenyl residue.

In another particular embodiment the invention provides a fine fragrance or consumer product, such as a personal care or household care composition that is perfumed by a compound represented by the formula

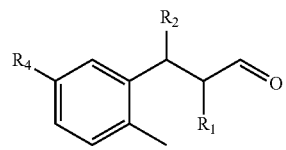

Formula 4 wherein
$R_1$ and $R_2$, each independently may represent H or methyl; and
$R_4$ represents an iso-butyl or sec-butyl group, or a saturated or unsaturated $C_5$-$C_7$ alkyl or alkenyl residue, which may be unsubstituted or substituted, optionally with cyclopropyl groups.

In another particular embodiment the invention provides a fine fragrance or consumer product, such as a personal care or household care composition that is perfumed by a compound represented by the formula

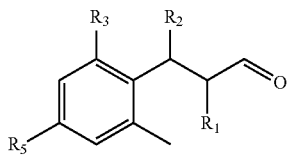

Formula 5 wherein
$R_1$, $R_2$, and $R_3$ each independently may represent H or methyl; and
$R_5$ is an iso-butyl or sec-butyl group, or a saturated or unsaturated $C_5$-$C_7$ alkyl or alkenyl residue, which may be unsubstituted or substituted, optionally with cyclopropyl groups.

In another particular embodiment the invention provides a fine fragrance or consumer product, such as a personal care or household care composition that is perfumed by a compound represented by the formula

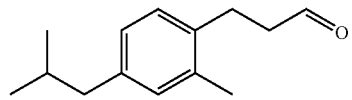

In yet more particular embodiments of the present invention there is provided a fine fragrance or consumer product, such as a personal care or household care composition that is perfumed by one or more compounds selected from 3-(4-isobutyl-2-methylphenyl)propanal, 3-(4-isobutyl-2,6-dimethylphenyl)propanal, 3-(4-isobutyl-2-methylphenyl)-2-methylpropanal, 3-(4-isobutyl-2-methylphenyl)butanal, 3-(4-(sec-butyl)-2-methylphenyl)propanal, 3-(2-methyl-4-(tert-pentyl)phenyl)propanal, 3-(4-isopentyl-2-methyl phenyl)propanal, 3-(2-methyl-4-(4-methylpentyl)phenyl)propanal, 3-(2-methyl-5-(4-methylpentyl)phenyl)propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl)phenyl)propanal, 3-(5-isobutyl-2-methylphenyl)propanal, 3-(2-methyl-4-(2-methylbutyl)phenyl)propanal, 5-isobutyl-2,3-dihydro-1H-indene-2-carbaldehyde, 3-(4-(tert-butyl)-2-methylphenyl)propanal, 3-(4-isopropyl-2-methylphenyl)propanal, 3-(1,1,6-trimethyl-2,3-dihydro-1H-inden-5-yl)propanal, 3-(2-methyl-5-(4-methylpentyl)phenyl)propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl)phenyl)propanal, 3-(5-Isobutyl-2-methylphenyl)propanal, 3-(4-isobutyl-2-methylphenyl)propanal, 3-(4-isobutyl-2,6-dimethylphenyl)propanal, 3-(4-isobutyl-2-methylphenyl)-2-methylpropanal, 3-(4-isobutyl-2-methylphenyl)butanal, 3-(4-(sec-butyl)-2-methylphenyl)propanal, 3-(2-methyl-4-(tert-pentyl)phenyl)propanal, 3-(4-isopentyl-2-methylphenyl)propanal and 3-(2-methyl-4-(4-methylpentyl)phenyl)propanal.

The compounds defined above, when added to a fine fragrance or consumer product, such as a personal care or household care composition, impart a characteristic muguet odour to said compositions. According to another aspect of the present invention there is provided a method of imparting muguet odour characteristics to a fine fragrance or consumer product, such as a personal care or household care composition comprising the step of adding to said composition a compound defined above or a perfume composition containing said compound.

In yet another aspect of the invention there is provided a method of imparting muguet odour characteristics to a fine fragrance or consumer product, such as a personal care or household care composition, comprising the step of selectively adding to said fine fragrance or consumer product an aryl-substituted alkanal compound defined above, and selectively excluding from said fine fragrance or consumer product any aryl-substituted alkanal compounds, which are unsubstituted on the ring at the position ortho to the substituent containing aldehyde functionality.

In yet another aspect of the invention there is provided a method of imparting muguet odour characteristics to a fine fragrance or consumer product, such as a personal care or household care composition, comprising the step of adding thereto an aryl-substituted alkanal compound defined above, and selectively excluding from said fine fragrance or consumer product any aryl-substituted alkanal compounds, which are unsubstituted on the ring at the position ortho to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives under test conditions, whereas said compounds being excluded on the basis that they do degrade to their benzoic acid derivatives under test conditions.

In yet another aspect of the invention there is provided a perfume composition comprising an aryl-substituted alkanal compound bearing a substituent on the aryl ring ortho to a substituent bearing the aldehyde functionality, in a suitable container, together with labelling that does not contain any CMR2 classification.

Consumer products, such as personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, and compositions to fine fragrance applications, as well as all manner of consumer product applications, such as personal and house hold care compositions and a very detailed description of such compositions is not warranted here. However, specific compositions that can be mentioned include cleaning compositions; autocare compositions; cosmetic compositions; textile treatment compositions; and air freshener and air care compositions.

Cleaning products include:—

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of H2 gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like; and Special-purpose cleaning products, examples being those for glass-ceramic hobs, and also carpet cleaners and stain removers.

Autocare products include:—

Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:—

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, shaving products, perfumes;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

Textile treatment products include:—

Detergents or fabric conditioners, for example, in either liquid or solid form.

Air fresheners and room fragrancers include:—

Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, *eucalyptus* oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

Consumer product compositions referred to hereinabove, particularly those for use in washing or cleaning applications may contain one or more of the following substances:

Builder substances, surfactants, enzymes, bleaching agents, such as preferably organic and/or inorganic peroxygen compounds, peroxygen activators, water-miscible organic solvents, sequestering agents, electrolytes, pH regulators, thickeners, and further adjuvants such as soil release active substances, optical brighteners, graying inhibitors, color transfer inhibitors, foam regulators, and dyes.

Surfactant include anionic surfactants, nonionic surfactants, and mixtures thereof, but also cationic surfactants, are appropriate. Suitable nonionic surfactants are, in particular, ethoxylation and/or propoxylation products of alkyl glycosides and/or of linear or branched alcohols each having 12 to 18 carbon atoms in the alkyl portion and 3 to 20, by preference 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 carbon atoms in the alkyl residue.

Suitable anionic surfactants include soaps, and those that contain sulfate or sulfonate groups having preferably alkali ions as cations. Soaps include alkali salts of the saturated or unsaturated fatty acids having 12 to 18 carbon atoms. Such fatty acids can also be used in incompletely neutralized form. Included among the usable surfactants of the sulfate type are the salts of the sulfuric acid semi-esters of fatty alcohols having 12 to 18 carbon atoms, and the sulfated products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants include esterquats and/or the quaternary ammonium compounds (QACs). QACs may be produced by the reaction of tertiary amines with alkylating agents such as methyl chloride, benzyl chloride, dimethyl sulfate, dodecyl bromide, but also ethylene oxide. The alkylation of tertiary amines having a long alkyl residue and two methyl groups occurs particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-C12-alkylammonium chloride), benzoxonium chloride (benzyl-dodecyl-bis(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_8$ to $C_{22}$ alkyl residues, in particular $C_{12}$ to $C_{14}$ alkylbenzyldimethylammonium chloride.

Esterquats include the commercially available methylhydroxyalkyldialkoyloxyalkylammonium methosulfates marketed by the Stepan company under the trademark Stepantex™, or the products of Cognis Deutschland GmbH known under the trade name Dehyquat™, or the Rewoquat™ products of Goldschmidt-Witco.

Surfactants may be employed in amounts of 5 wt % to 50 wt % in a consumer product of the present invention.

Builders include the water-soluble and/or water-insoluble, organic and/or inorganic builders. In particular, they include the water-soluble organic builder substances are polycarboxylic acids, more particularly citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain small proportions of polymerizable substances having no carboxylic-acid functionality. The relative molecular weight of homopolymers of unsaturated carboxylic acids is generally between 5000 and 200,000, that of the copolymers between 2000 and 200,000, based in each case on free acid. Suitable compounds of this class are copolymers of acrylic acid or methacrylic acid with vinyl ethers, such as vinylmethyl ethers, vinyl esters, ethylene, propylene, and styrene, in which the proportion of acid is equal to at least 50 wt %. It is also possible to use, as water-soluble organic builder substances, terpolymers that contain two unsaturated acids and/or salts thereof as monomers and, as a third monomer, vinyl alcohol and/or a vinyl alcohol derivative or a carbohydrate. The first acid monomer or salt thereof may be derived from an ethylenically mono-unsaturated $C_3$ to $C_8$ carboxylic acid. The second acid monomer or salt thereof can be a derivative of a $C_4$ to $C_8$ dicarboxylic acid, for example maleic acid. The third monomeric unit is constituted by vinyl alcohol and/or an esterified vinyl alcohol. Polymers may contain 60 wt % to 95 wt %, in particular 70 wt % to 90 wt %, (meth)acrylic acid or (meth)acrylate, as well as 5 wt % to 40 wt % vinyl alcohol and/or vinyl acetate. Particular polymers are those in which the weight ratio of (meth)acrylic acid respectively (meth) acrylate to maleic acid or maleate is between 1:1 and 4:1. Both the quantities and the weight ratios are based on the acids. The second acid monomer or salt thereof can also be a derivative of an allylsulfonic acid that is substituted in the 2-position with an alkyl radical, e.g. a $C_1$ to $C_4$ alkyl radical, or with an aromatic radical that may be derived from benzene or benzene derivatives. Terpolymers may contain 40 wt % to 60 wt %, in particular 45 to 55 wt %, (meth) acrylic acid or (meth)acrylate, particularly preferably acrylic acid or acrylate, 10 wt % to 30 wt %, by preference 15 wt % to 25 wt % methallylsulfonic acid or methallylsulfonate, and as a third monomer 15 wt % to 40 wt %, by preference 20 wt % to 40 wt % of a carbohydrate. This carbohydrate can be, for example, a mono-, di-, oligo-, or poly-saccharide, e.g. sucrose. The terpolymers generally have a relative molecular weight between 1000 and 200,000. Further copolymers include those that comprise, as monomers, acrolein and acrylic acid/acrylic acid salts, or vinyl acetate. Especially for the manufacture of liquid detergents, the organic builder substances can be used in the form of aqueous solutions, for example a 30- to 50-weight-percent aqueous solutions. All the aforesaid acids may be used in the form of their water-soluble salts, in particular their alkali salts.

Organic builder substances can be employed in quantities of up to 40 wt %.

Water-soluble inorganic builder materials include alkali silicates and polyphosphates, e.g. sodium triphosphate. Crystalline or amorphous alkali aluminosilicates, e.g. crystalline sodium aluminosilicates, may also be employed as water-insoluble, water-dispersible inorganic builder materials, in quantities of up to 50 wt %, for example. Aluminosilicates typically comprise particles having a particle size less than 30 µm.

Crystalline alkali silicates may also be employed, either alone or used with amorphous silicates. The alkali silicates usable in consumer products of the present invention as detergency builders may have a molar ratio of alkali oxide to $SiO_2$ below 0.95, in particular from 1:1.1 to 1:12, and can be present in amorphous or crystalline fashion. The alkali silicates may be sodium silicates, in particular the amorphous sodium silicates, having a $Na_2O:SiO_2$ molar ratio from 1:2 to 1:2.8.

Builder substances may be contained in consumer product compositions according to the present invention at levels up to 60 wt %.

Peroxygen compounds include organic peracids or peracid salts of organic acids such as phthalimidopercapronic acid, perbenzoic acid, or salts of diperdodecanedioic acid, hydrogen peroxide, and inorganic salts that release hydrogen peroxide under application conditions, such as perborate, percarbonate, and/or persilicate. If solid peroxygen compounds are to be used, they can be utilized in the form of powders or granulates, which in principle can also be encased in known fashion.

Peroxygen compounds may be employed in amounts up to 50 wt %. The addition of small quantities of known bleaching-agent stabilizers, for example phosphonates, borates respectively metaborates, and metasilicates, as well as magnesium salts such as magnesium sulfate, may be useful.

Compounds that, under perhydrolysis conditions, yield aliphatic peroxocarboxylic acids having preferably 1 to 10 carbon atoms, in particular 2 to 4 carbon atoms, and/or (optionally substituted) perbenzoic acid, can be used as bleach activators. Substances that carry O- and/or N-acyl groups having the aforesaid number of carbon atoms, and/or optionally substituted benzoyl groups, are suitable. Multiple acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof (SORMAN), acylated sugar derivatives, in particular pentaacetylglucose (PAG), pentaacetylfructose, tetraacetylxylose and octaacetyllactose, as well as acetylated, optionally N-alkylated glutamine and gluconolactone, and/or N-acylated lactams, for example N-benzoylcaprolactam, may be employed. Hydrophilically substituted acyl acetates and acyl lactams may likewise be employed. Combinations of conventional bleach activators can also be used. Such bleach activators can be contained in the usual quantity range, by preference in quantities from 1 wt % to 10 wt %, in particular 2 wt % to 8 wt %, based on the entire agent.

In addition to or instead of the aforementioned conventional bleach activators, sulfonimines and/or bleach-intensifying transition metal salts or transition metal complexes can also be contained as bleach catalysts. Included among the appropriate transition metal compounds are, in particular, salen complexes of manganese, iron, cobalt, ruthenium, or molybdenum and nitrogen-analog compounds thereof, carbonyl complexes of manganese, iron, cobalt, ruthenium, or molybdenum, complexes of manganese, iron, cobalt, ruthenium, molybdenum, titanium, vanadium, and copper having nitrogen-containing tripod ligands, amine complexes of cobalt, iron, copper, and ruthenium. Combinations of bleach activators and transition metal bleach catalysts can likewise be used. Bleach-intensifying transition metal complexes, in particular having the central atoms Mn, Fe, Co, Cu, Mo, V, Ti, and/or Ru, can be used in conventional quantities, such as up to 1 wt % based on the weight of the consumer product composition.

Suitable enzymes that may be employed in compositions are those from the class of the proteases, cutinases, amylases, pullulanases, hemicellulases, cellulases, lipases, oxidases, and peroxidases, as well as mixtures thereof. Enzymatically active substances recovered from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia*, are also suitable. The enzymes that are used as applicable can be adsorbed onto carrier substances and/or embedded into encasing substances in order to protect them from premature inactivation. They may be contained in washing products according to the present invention in amounts typically below 5 wt %.

Optical brighteners include derivatives of diaminostilbenedisulfonic acid or alkali metal salts thereof. Suitable, for example, are salts of 4,4'-bis(2-anilino-4-morpholino-1,3,5-triazinyl-6-amino)stilbene-2,2'-disulfonic acid, or compounds of similar structure that carry, instead of the morpholino group, a diethanolamino group, a methylamino group, an anilino group, or a 2-methoxyethylamino group. Brighteners of the substituted diphenylstyryl type can also be present, e.g. the alkali salts of 4,4'-bis(2-sulfostyryl) diphenyl, of 4,4'-bis(4-chloro-3-sulfostyryl)diphenyl, or of 4-(4-chlorostyryl)-4'-(2-sulfostyryl)diphenyl. Mixtures of the aforesaid optical brighteners can also be used.

Foam inhibitors include organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, can also be employed. The foam inhibitors, in particular silicone- and/or paraffin-containing foam inhibitors are by preference bound to a granular carrier substance that is soluble or dispersible in water. Mixtures of paraffins and bistearylethylenediamide, in particular may be employed.

Soil release active substances are those compounds that positively influence the ability of oils and fats to be washed out of textiles. This effect becomes particularly apparent when the soiled textile is one that has already been previously washed several times with a washing agent according to the present invention that contains this oil- and fat-releasing component. The preferred oil- and fat-releasing components include, for example, nonionic cellulose ethers such as methyl cellulose and methylhydroxypropyl cellulose having a 15 to 30 wt % proportion of methoxy groups and a 1 to 15 wt % proportion of hydroxypropyl groups, based in each case on the nonionic cellulose ethers, as well as polymers, known from the existing art, of phthalic acid and/or terephthalic acid resp. of their derivatives with monomeric and/or polymeric diols, in particular polymers of ethylene terephthalates and/or polyethylene glycol terephthalates or anionically and/or nonionically modified derivatives thereof.

Colour transfer inhibitors include polymers of vinylpyrrolidone, vinyl imidazole, vinylpyridine-N-oxide, or copolymers thereof. Also usable are both polyvinylpyrrolidones having molecular weights from 15,000 to 50,000 and polyvinylpyrrolidones having molecular weights above 1,000,000, in particular from 1,500,000 to 4,000,000, N-vinylimidazole/N-vinylpyrrolidone copolymers, polyvinyloxazolidones, copolymers based on vinyl monomers and carboxylic acid amides, pyrrolidone-group-containing polyesters and polyamides, grafted polyamidoamines and polyethylenimines, polymers having amide groups made up of secondary amines, polyamine-N-oxide polymers, polyvinyl alcohols, and copolymers based on acrylamidoalkenyl sulfonic acids. It is also possible, however, to use enzymatic systems encompassing a peroxidase and hydrogen peroxide or a substance that yields hydrogen peroxide in water.

Graying inhibitors are those materials that keep dirt that has been detached from the textile fibers suspended in a washing medium. Water-soluble colloids, usually organic in nature, are suitable for this, for example starch, size, gelatin, salts of ethercarboxylic or ethersulfonic acids of starch or of cellulose, or salts of acid sulfuric acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof may be used, for example in quantities from 0.1 to 5 wt % based on the weight of the consumer product.

Organic solvents include alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind are present in washing products according to the present invention in amounts typically not exceeding 30 wt %.

pH regulators include citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are contained in the agents according to the present invention in quantities preferably not above 20 wt %, in particular from 1.2 wt % to 17 wt %.

The compounds are may be particularly used to perfume household products containing enzymes, such as those defined above, and in particular textile treatment products, such as detergents, containing enzymes.

There now follows a series of examples that serve to further illustrate the invention.

Example 1

Synthesis of 3-(4-isobutyl-2-methylphenyl)propanal

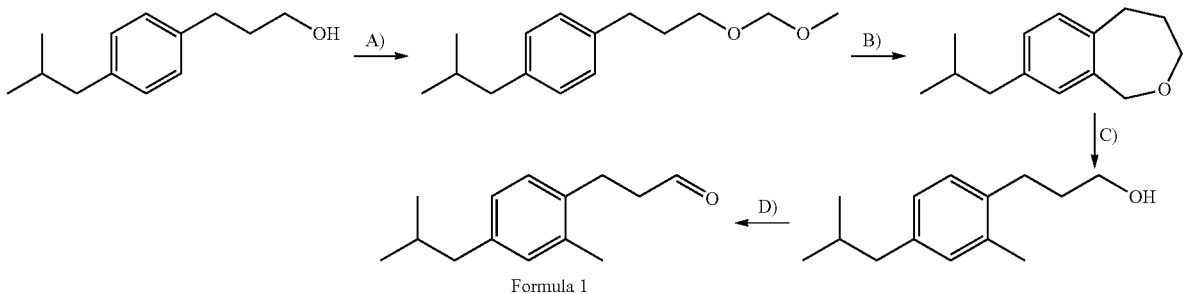

Formula 1

A) 1-Isobutyl-4-(3-(methoxymethoxy)propyl)benzene

To a solution of 3-(4-isobutylphenyl)propan-1-ol (641.0 g, 3.33 mol) in 1.5 L of dimethoxymethane was added lithium bromide (14.5 g) and p-toluene sulfonic acid (10.0 g). The mixture was stirred for 20 h at room temperature and then poured with stirring into aqueous sodium hydroxide (200 ml, 2M). The organic phase was washed neutral with a diluted solution of NaCl, dried (MgSO$_4$) and evaporated in vacuo to yield 1-isobutyl-4-(3-(methoxymethoxy)propyl)benzene (721.0 g, 91.5%) as a colourless oil. $^1$H-NMR (400 MHz, CDCl3): δ=7.17-7.08 (m, 4H), 4.68 (s, 2H), 3.59 (t, J=6.4 Hz, 2H), 3.42 (s, 3H), 2.74 (t, J=7.8 Hz, 2H), 2.49 (d, J=7.1 Hz, 2H), 2.0-1.84 (m, 3H), 0.95 (d, J=6.6 Hz, 6H) ppm. $^{13}$C-NMR (400 MHz, CDCl3): δ=139.5 (s), 139.4 (s), 129.5 (d, 2C), 128.5 (d, 2C), 96.9 (t), 67.6 (t), 55.6 (q), 45.5 (t), 32.5 (t), 31.9 (t), 30.7 (d), 22.8 (q, 2C) ppm. GC/MS (EI): 236 (M$^+$), 204 (29), 161 (65), 147 (59), 131 (100), 117 (49), 105 (37), 104 (26), 91 (46), 57 (29), 45 (64).

B) 8-Isobutyl-1,3,4,5-tetrahydrobenzo[c]oxepine

To a cooled solution (0° C.) of AlCl$_3$ (10.33 g) in dichlormethane (80 ml) was added dropwise a solution of 1-isobutyl-4-(3-(methoxymethoxy)propyl)benzene (13.9 g, 55.36 mmol) in dichloromethane (40 ml). After the addition was complete, the mixture was stirred for 1.5 h at 5° C. and poured into an aqueous sodium hydroxide solution (80 ml, 2M). The mixture was extracted with MTBE and the organic phases were washed with after and brine, dried (MgSO$_4$) and evaporated in vacuo to afford a clear yellowish oil (11.91 g) which was first distilled in kugelrohr (125° C., 0.12 mbar) and then purified by chromatography to yield 8-isobutyl-1,3,4,5-tetrahydrobenzo[c]oxepine (6.95, 61%) as a colourless oil. Odor: $^1$H NMR (400 MHz, CDCl$_3$): δ=7.11 (d, J=7.33 Hz, 1H), 7.01-6.97 (m, 2H), 4.66 (s, 2H), 4.09-4.06 (m, 2H), 3.02-2.98 (m, 2H), 2.46 (d, J=7.33 Hz, 2H), 1.93-1.82 (m, 1H), 0.94 (d, J=6.8 Hz, 6H) ppm. $^{13}$C-NMR (400 MHz, CDCl$_3$): δ=140.3 (s), 140.05 (s), 139.9 (s), 129.8 (d), 129.3 (d), 128.8 (d), 76.1 (t), 75.6 (t), 45.3 (t), 35.5 (t), 30.9 (t), 30.6 (d), 22.8 (q, 2C) ppm. GC/MS (EI): 204 (M$^+$, 33), 161 (100), 147 (44), 143 (58), 131 (31), 129 (28), 119 (61), 115 (34), 105 (43), 91 (34).

C) 3-(4-Isobutyl-2-methylphenyl)propan-1-ol

A catalytic amount of borontriflouride etherate (0.3 g) was added to a suspension of Pd/C (10%, 0.5 g) and 8-isobutyl-1,3,4,5-tetrahydrobenzo[c]oxepine (50.0 g, 244.7 mmol). The mixture was hydrogenated in an autoclave for 2 h at 9 bar and 50° C. The suspension was filtered and thin film distilled (160° C., 0.11 mbar) to yield 3-(4-isobutyl-2-methylphenyl)propan-1-ol (45.4 g, 89.9%) as a viscous colourless oil. Odour: $^1$H-NMR (400 MHz, CDCl$_3$): δ=7.10 (d, J=7.6 Hz, 1H), 6.99-6.94 (m, 2H), 3.75 (t, J=6.6 Hz, 2H), 2.74-2.68 (m, 2H), 2.47 (d, J=7.3 Hz, 2H), 2.34 (s, 3H), 2.19 (s, 1H, —OH), 1.95-1.84 (m, 1H), 0.96 (d, J=6.6 Hz, 6H) ppm. $^{13}$C-NMR (400 MHz, CDCl3): δ=139.7 (s), 137.6 (s), 135.9 (s), 131.5 (d), 128.9 (d), 127.1 (d), 63.0 (t), 45.4 (t), 33.5 (t), 30.6 (d), 29.5 (t), 22.9 (q), 19.7 (q) ppm. GC/MS (EI): 206 (M$^+$, 25), 163 (100), 161 (27), 145 (84), 119 (53), 117 (33), 115 (32), 105 (41), 91 (40), 41 (23).

D) 3-(4-Isobutyl-2-methylphenyl)propanal

Pyridinium chlorochromate (PCC, 37.6 g, 174.49 mmol) was added portionwise to a solution of 3-(4-isobutyl-2-methylphenyl)propan-1-ol (30.0 g, 145.41 mmol) in dichloromethane (300 ml); the temperature rose to 35° C. The mixture was stirred for 1 h and another portion of PCC (10 g, 46.4 mmol) was added and stirring was continued for another 15 min. The reaction mixture was filtered over Florisil and silica gel. The filtrate was evaporated in vacuo (23.2 g) and distilled in kugelrohr (143° C., 0.08 mbar) to yield 3-(4-isobutyl-2-methylphenyl)propanal (19.01 g, 64%) as a colorless oil. Odor: floral, aldehydic, green, Lilial, watery. $^1$H-NMR (400 MHz, CDCl3): δ=9.88 (t, J=1.5 Hz, 1H), 7.07 (d, J=7.6 Hz, 1H), 7.0-6.95 (m, 2H), 2.98-2.93 (m, 2H), 2.79-2.74 (m, 2H), 2.46 (d, J=7.1 Hz, 2H), 2.33 (s, 3H), 1.95-1.82 (m, 1H), 0.95 (d, J=6.6 Hz, 6H) ppm. $^{13}$C-NMR (400 MHz, CDCl3): δ=202.2 (d), 140.2 (s), 136 (s), 135.9 (s), 131.6 (d), 128.6 (d), 127.3 (d), 45.4 (t), 44.6 (t), 30.6 (d), 25.5 (t), 22.9 (q), 19.7 (q) ppm. GC/MS (EI): 204 (M$^+$, 23), 161 (100), 147 (26), 143 (49), 119 (84), 118 (34), 117 (33), 115 (33), 105 (59), 91 (36).

The following compounds were prepared according to the sequence described in Example 1

Example 2

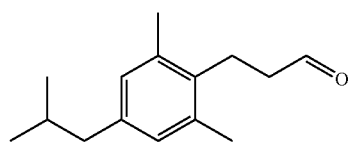 [SMILES: Cc1cc(CC(C)C)cc(C)c1CCC=O]

3-(4-Isobutyl-2,6-dimethylphenyl)propanal

Odor: floral, aldehydic, fruity, slightly rosy $^1$H NMR (400 MHz, CDCl$_3$): δ=9.91-9.89 (t, J=1.5 Hz, 1H), 6.84 (s, 2H), 2.99-2.93 (m, 2H), 2.67-2.61 (m, 2H), 2.42-2.39 (d, J=7.1 Hz, 2H), 2.32 (s, 6H), 1.94-1.80 (m, 1H), 0.96-0.92 (d, J=6.57, 6H) ppm. $^{13}$C NMR (400 MHz, CDCl$_3$): δ=202.1 (d), 139.9 (s), 136.0 (s, 2C), 134.5 (s), 129.6 (d, 2C), 45.4 (t), 43.6 (t), 30.5 (d), 22.9 (q, 2C), 22.1 (t), 20.1 (q, 2C) ppm. GC/MS (EI): 218 (M$^+$), 175 (81), 162 (31), 157 (55), 133 (71), 132 (29), 119 (100), 117 (29), 115 (37), 105 (31), 91 (47).

Example 3

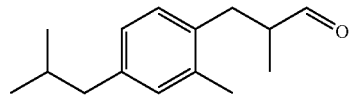 [SMILES: Cc1cc(CC(C)C)ccc1CC(C)C=O]

3-(4-Isobutyl-2-methylphenyl)-2-methylpropanal

Odor: fatty, watery, floral, green, aldehydic $^1$H NMR (400 MHz, CDCl$_3$): δ=9.75 (d, J=1.8 Hz, 1H), 7.03 (d, J=7.6 Hz, 1H), 6.99-6.92 (m, 2H), 3.09 (dd, J=6.1 Hz, 13.9 Hz, 1H), 2.73-2.73 (m, 1H), 2.61-2.54 (m, 1H), 2.44 (d, J=7.1 Hz, 2H), 2.32 (s, 3H), 1.94-1.81 (m, 1H), 1.14 (d, J=6.8 Hz, 3H), 0.93 (d, J=6.6 Hz, 6H) ppm. $^{13}$C NMR (400 MHz, CDCl$_3$): δ=204.9 (d), 140.3 (s), 136.1 (s), 134.6 (s), 131.7 (d), 129.8 (d), 127.1 (d), 47.3 (d), 45.4 (t), 34.0 (t), 30.6 (d), 22.8 (q), 19.9 (q), 13.9 (q) ppm. GC/MS (EI): 218 (M$^+$), 161 (100), 119 (62), 118 (24), 117 (23), 115 (23), 106 (16), 105 (81), 91 (31), 43 (27), 41 (25).

Example 4

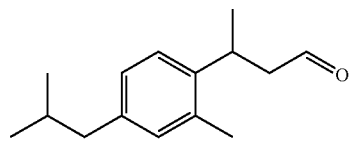 [SMILES: Cc1cc(CC(C)C)ccc1C(C)CC=O]

3-(4-Isobutyl-2-methylphenyl)butanal

Odor: floral, green, watery, fatty $^1$H NMR (400 MHz, CDCl$_3$): δ=9.74 (t, J=1.8 Hz, 1H), 7.10 (d, J=7.8 Hz, 1H), 6.01-6.95 (m, 2H), 3.64-3.55 (m, 1H), 2.77 (ddd, J=1.8 Hz, 6.7 Hz, 16.7 Hz, 1H), 2.67 (ddd, J=2.2 Hz, 8.1 Hz, 16.5 Hz, 1H), 2.43 (d, J=7.3 Hz, 2H), 2.37 (s, 3H), 1.92-1.82 (m, 1H), 1.30 (d, J=6.8 Hz, 3H), 0.93 (d, J=6.8 Hz, 6H) ppm. $^{13}$C NMR (400 MHz, CDCl$_3$): δ=202.5 (d), 141.1 (s), 139.9 (s), 135.0 (s), 131.8 (d), 127.5 (d), 125.4 (d), 51.7 (t), 45.4 (t), 30.6 (d), 29.5 (d), 22.9 (q), 22.6 (q), 19.8 (q) ppm. GC/MS (EI): 218 (M$^+$), 175 (100), 161 (25), 133 (43), 131 (28), 119 (22), 117 (28), 115 (25), 105 (16), 105 (61), 91 (28), 41 (21).

Example 5

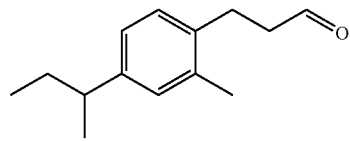

3-(4-(sec-Butyl)-2-methylphenyl)propanal

Odor: green, floral, marine, Lilial-like $^1$H NMR (400 MHz, CDCl$_3$): δ=9.89 (t, J=1.5 Hz, 1H), 7.08 (d, J=7.3 Hz, 1H), 7.02-6.98 (m, 2H), 2.98-2.93 (m, 2H), 2.80-2.74 (m, 2H), 2.56 (m, J=7.1 Hz, 1H), 2.34 (s, 3H), 1.67-1.56 (m, 2H), 1.26 (d, J=6.8 Hz, 3H), 0.87 (t, J=7.5 Hz, 3H) ppm. $^{13}$C NMR (400 MHz, CDCl$_3$): δ=202.2 (d), 146.3 (s), 136.1 (s), 136.0 (s), 129.6 (d), 128.7 (d), 125.2 (d), 44.5 (t), 41.6 (d), 31.6 (t), 25.5 (t), 22.2 (q), 19.8 (q), 12.7 (q) ppm. GC/MS (EI): 204 (M$^+$), 175 (100), 147 (14), 133 (16), 131 (54), 119 (32), 117 (26), 115 (27), 105 (27), 91 (35), 77 (14).

Example 6

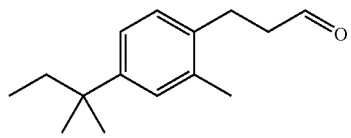 [SMILES: CCC(C)(C)c1ccc(CCC=O)c(C)c1]

3-(2-Methyl-4-(tert-pentyl)phenyl)propanal

Odor: floral, green, weak
$^1$H NMR (400 MHz, CDCl$_3$): δ=9.89 (t, J=1.5 Hz, 1H), 7.16-7.07 (m, 3H), 2.99-2.93 (m, 2H), 2.80-2.74 (m, 2H), 2.35 (s, 3H), 1.67 (q, J=7.6 Hz, 2H), 1.30 (s, 6H), 0.74 (t, J=7.6 Hz, 3H) ppm. $^{13}$C NMR (400 MHz, CDCl$_3$): δ=202.2 (d), 148.1 (s), 135.6 (s), 128.4 (d, 2C), 124.2 (d), 44.5 (t), 37.9 (s), 37.2 (t), 28.8 (q, 2C), 25.4 (t), 20.1 (q), 9.6 (q) ppm. GC/MS (EI): 218 (M$^+$), 190 (15), 189 (100), 145 (42), 131 (15), 129 (10), 128 (11), 115 (16), 105 (16), 91 (18), 41 (12).

Example 7

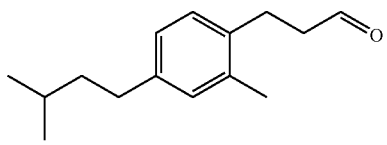 [SMILES: Cc1cc(CCC(C)C)ccc1CCC=O]

3-(4-Isopentyl-2-methyl phenyl)propanal

Odor: aldehydic, floral, green, watery
$^1$H NMR (400 MHz, CDCl$_3$): δ=9.87 (t, J=1.5 Hz, 1H), 7.06 (d, J=7.8 Hz, 1H), 7.02-6.97 (m, 2H), 2.96-2.91 (m, 2H), 2.78-2.72 (m, 2H), 2.60-2.54 (m, 2H), 2.32 (s, 3H), 1.67-1.55 (m, 1H), 1.54-1.46 (m, 2H), 0.96 (d, J=6.6, 6H) ppm. $^{13}$C NMR (400 MHz, CDCl$_3$): δ=202.2 (d), 141.7 (s), 136.1 (s), 135.9 (s), 130.9 (d), 128.8 (d), 126.5 (d), 44.6 (t), 41.3 (t), 33.7 (t), 28.1 (d), 25.5 (t), 22.9 (q, 2C), 19.7 (q) ppm. GC/MS (EI): 218 (M$^+$), 119 (37), 118 (100), 117 (23), 115 (22), 106 (31), 105 (36), 91 (28), 43 (22), 41 (29), 29 (20).

Example 8

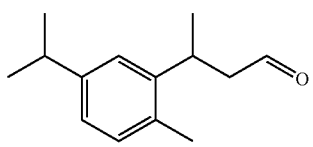

3-(5-Isopropyl-2-methylphenyl)butanal

Odor: floral fruity, slightly rosy, slightly green
$^1$H NMR (400 MHz, CDCl$_3$): δ=9.77 (dd, J=1.8 Hz, 2.2 Hz, 1H), 7.13 (d, J=7.8 Hz, 1H), 7.09-7.02 (m, 2H), 3.69-3.59 (m, 1H), 2.92 (sp, J=6.8 Hz, 1H), 2.81 (ddd, J=1.7 Hz, 6.2 Hz, 16.6 Hz, 1H), 2.72 (ddd, J=2.2 Hz, 8.3 Hz, 16.7 Hz, 1H), 2.38 (s, 3H), 1.34 (d, J=6.8 Hz, 3H), 1.29 (d, J=6.8 Hz, 6H) ppm. $^{13}$C NMR (400 MHz, CDCl$_3$): δ=202.3 (d), 147.4 (s), 143.8 (s), 132.8 (s), 130.9 (d), 124.5 (d), 123.9 (d), 51.6 (t), 34.3 (d), 29.8 (d), 24.5 (q), 21.9 (q), 19.4 (q) ppm. GC/MS (EI): 204 (M$^+$), 161 (54), 147 (27), 145 (38), 119 (100), 117 (25), 115 (32), 105 (43), 91 (42), 43 (31), 41 (31).

Example 9

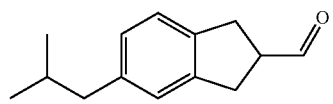

5-Isobutyl-2,3-dihydro-1H-indene-2-carbaldehyde

Odor: aldehydic, marine, watery, floral
$^1$H NMR (400 MHz, CDCl$_3$): δ=9.80 (d, J=1.8 Hz, 1H), 7.15 (d, J=7.6 Hz, 1H), 7.04 (s, 1H), 6.98 (d, J=7.3 Hz, 1H), 3.34-3.25 (m, 3H), 3.24-2.96 (m, 2H), 2.47 (d, J=7.1 Hz, 2H), 1.93-1.73 (m, J=6.82, 1H), 0.93 (d, J=6.6H, 6H) ppm. $^{13}$C NMR (400 MHz, CDCl$_3$): δ=203.4 (d), 141.5 (s), 140.9 (s), 138.7 (s), 128.2 (d), 125.7 (d), 124.5 (d), 51.3 (d), 45.7 (t), 33.3 (t), 33.0 (t), 30.7 (d), 22.8 (q, 2C) ppm. GC/MS (EI): 202 (M$^+$ 35), 159 (100), 145 (32), 141, (47), 131 (17), 129 (91), 128 (70), 127 (23), 115 (43), 41 (21).

Example 10

Synthesis of
3-(2-Methyl-4-(4-methylpentyl)phenyl)propanal

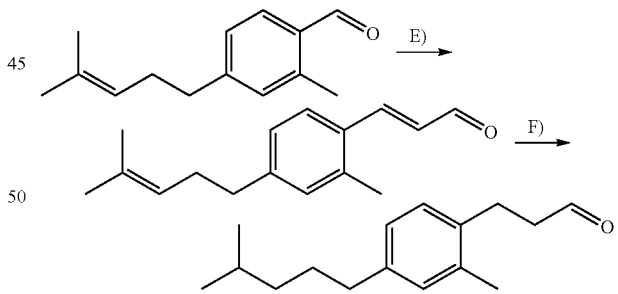

E) (E)-3-(2-methyl-4-(4-methylpent-3-en-1-yl)phenyl)acrylaldehyde

To a solution of 2-methyl-4-(4-methylpent-3-en-1-yl)benzaldehyde (3.0 g, 14.8 mmol) and trimethylorthoformate (2.36 g, 22.3 mmol) in methanol (2 ml) at 0° C., was added acetyl chloride (0.05 g, 0.64 mmol). The mixture was stirred at room temperature for 30 min and then aqueous sodium bicarbonate (2.0 ml) was added. The organic layer was separated, concentrated and dissolved again in diethyl ether (2.0 ml). Borontrifluoride etherate (0.11 g, 0.74 mmol) was added dropwise followed by ethoxyethene (1.40 g, 19.3 mmol). The reaction mixture was stirred at room temperature for 30 min, aqueous sodium bicarbonate (2.0 ml) was added, and the organic layer was separated. The organic layer was dried (MgSO₄). The solvent was evaporated in vacuo and aqueous HCl solution (7.4%, 5.0 ml) was added to the residue. The mixture was heated to reflux for 5 h and then cool to room temperature. The reaction was diluted by water (15 ml) and then extracted by MTBE (2×15 ml). The organic layers were dried over MgSO₄ and evaporated in vacuo. The crude product was purified by column chromatography to yield (E)-3-(2-methyl-4-(4-methylpent-3-en-1-yl)phenyl)acrylaldehyde (1.1 g, 32.5%) as a colourless oil. ¹H-NMR (300 MHz, CDCl₃): δ=9.70 (d, J=7.7 Hz, 1H, CHO), 7.75 (d, J=15.7 Hz, 1H, Ar—CH=CH—), 7.57-7.50 (m, 1H, Ar—H), 7.12-7.03 (m, 2H, Ar—H), 6.65 (dd, J=7.7 Hz, 15.7 Hz, 1H, =CH—CHO), 5.15 (t, J=6.4 Hz, 1H), 2.62 (t, J=7.8 Hz, 2H), 2.46 (s, 3H, Ar—CH₃), 2.33-2.25 (m, 2H), 1.69 (s, 3H, CH₃), 1.57 (s, 3H, CH₃) ppm. ¹³C-NMR (300 MHz, CDCl3): δ=193.9 (d), 150.4 (d), 146.1 (s), 137.9 (s), 132.5 (s), 131.2 (d), 130.3 (s), 128.7 (d), 126.9 (d), 126.8 (d), 123.3 (d), 36.0 (t), 29.7 (t), 25.7 (q), 19.8 (q), 19.7 (q) ppm. GC/MS (EI): 228 (22, M⁺), 213 (22), 200 (1), 185 (2), 171 (4), 160 (100), 145 (34), 131 (28), 115 (27), 103 (4), 91 (20), 79 (8), 69 (75), 53 (6), 41 (36).

f) 3-(2-Methyl-4-(4-methylpentyl)phenyl)propanal

In a 100 mL round-bottomed flask was added (E)-3-(2-methyl-4-(4-methylpent-3-en-1-yl)phenyl)acrylaldehyde (1.0 g, 2.9 mmol) in ethyl acetate (15 ml) to give a colorless solution. The solution was de-gased and purged with argon. Palladium on charcoal (0.1 g, Pd content of 10%) was added. The reaction was stirred under hydrogen atmosphere for 2 h until completion of the conversion (confirmed by GC). The reaction mixture was filtered through a small pad of silica gel and the solid was rinsed with ethyl acetate. The filtrate was collected and concentrated. The residue obtained was distilled by Kugelrohr to give 0.8 g of 3-(2-Methyl-4-(4-methylpentyl)phenyl)propanal as a colorless liquid. Odor: floral, green, watery. ¹H NMR (CDCl₃): δ=9.85-9.80 (m, 1H, CHO), 7.09-6.80 (m, 3 H, Ar—H), 2.89 (t, J=7.3 Hz, 2 H, Ar—CH₂—CH₂—CHO), 2.71 (t, J=7.3 Hz, 2 H, Ar—CH₂—CH₂—CHO), 2.51 (t, J=7.8 Hz, 2 H, Ar—CH₂—CH₂—CH₂), 2.28 (s, 3 H, Ar—CH₃), 1.70-1.50 (m, 3 H, (CH₃)₂CH—CH₂—CH₂—), 1.32-1.15 (m, 2 H, Ar—CH₂—CH₂—CH₂—), 0.87 (d, J=6.5 Hz, 6 H, 2 CH₃). ¹³C NMR (CDCl₃): δ=201.8 (d), 141.1 (s), 135.7 (s), 135.6 (s), 130.5 (d), 128.4 (d), 126.1 (d), 44.2 (t), 38.8 (t), 35.8 (t), 29.5 (t), 27.9 (d), 25.1 (t), 22.6 (q), 19.3 (q). MS: m/z (%)=232 (89) [M⁺], 214 (80), 204 (4), 189 (100), 176 (21), 161 (68), 147 (84), 129 (40), 119 (87), 105 (90), 91 (44), 77 (15), 65 (7), 55 (15), 43 (27).

Example 11

Synthesis of 3-(2-Methyl-5-(4-methylpentyl)phenyl)propanal

G) (E)-2-Bromo-1-methyl-4-(4-methylpent-1-en-1-yl)benzene

Preparation of the Grignard Reagent:

In a 250 mL three-necked flask was added magnesium turnings (2.44 g, 100 mmol), and 10 mL of anhydrous ether. Under argon atmosphere, with vigorous stirring was added 1-bromo-3-methylbutane (15.2 g in 50 mL ether) dropwise. Initially, 5 mL was added in order to initiate the reaction and the reaction temperature increased from RT to 40° C. Then the reaction mixture was cooled to 5 degree by an ice-water bath. With vigorously stirring, the rest of 1-bromo-3-methylbutane was added dropwise in half an hour. After completion of the addition, the reaction was refluxed for half an hour.

The Grignard Addition and Dehydration:

In a 250 mL three-necked flask was added 3-bromo-4-methylbenzaldehyde (10 g, 50 mmol) in ether (25 mL). Under argon atmosphere, the reaction mixture was cooled to 5 degree in an ice-water bath. The Grignard reagent prepared above was transferred into a 250 mL dropping funnel and was slowly added to the reaction mixture with vigorous stirring. The addition took 60 min during which time the reaction temperature was kept below 15° C. After completion of the addition, the reaction was heated to reflux for 10 min. The reaction mixture was cooled to 5 degree again. Then sat. NH₄Cl (aq. 75 mL) was added dropwise to quench the reaction. The organic layer was separated and the aqueous layer was extracted by ether (50 mL). The combined organic layers were washed once with brine (25 mL) and then dried with MgSO₄. The Solvent was evaporated to give a light yellow liquid which was transferred to a 250 mL round-bottomed flask and dissoved in toluene (100 ml). Then 4-methylbenzenesulfonic acid hydrate (0.87 g, 5.0 mmol) was added. Under argon atmosphere, the reaction mixture was refluxed via a Dean-Stark to remove water (oil bath temperature 135 degree). After 2 h, all water had been removed. GC analysis indicated completion of the conversion. The reaction was allowed to cool to room temperature. Then a slurry of NaHCO₃ salts (4.0 g) in water was added with vigorous stirring. After 10 min, the reaction was filtered and the solid was rinsed twice with toluene. The filtrate was collected and concentrated to give a yellowish liquid (39.8 g). The yellow liquid was further purified by Kugelrohr distillation to give 11.6 g of (E)-2-bromo-1-methyl-4-(4-methylpent-1-en-1-yl)benzene as a colorless liquid. ¹H NMR (CDCl₃): δ=7.43 (s, 1 H, Ar—H), 7.15-7.01 (m, 2 H, Ar—H), 6.21-6.02 (m, 2 H), 2.27 (s, 3H, Ar—CH₃), 1.99 (dd, J=6.6 Hz, 6.6 Hz, 2 H, —CH₂—), 1.72-1.56 (m, 1 H), 0.84 (d, J=6.6 Hz, 6 H, 2CH₃). ¹³C NMR (CDCl₃): δ=137.5 (s), 136.0 (s), 130.7 (d), 130.5 (d), 129.6 (d), 129.3 (d), 125.1

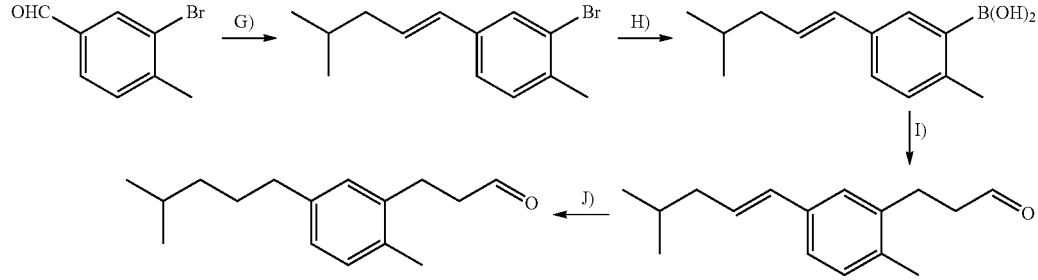

(s), 124.8 (d), 42.4 (t), 28.6 (d), 22.6 (q), 22.4 (q). MS: m/z (%)=252 (15) [M⁺], 209 (12), 196 (15), 130 (100), 115 (22), 77 (4), 63 (3), 51 (3), 41 (3).

H) (E)-(2-Methyl-5-(4-methylpent-1-en-1-yl)phenyl)boronic acid

To a solution of (E)-2-bromo-1-methyl-4-(4-methylpent-1-en-1-yl)benzene (11.6 g, 46 mmol) in THF (50 mL) which was cooled to −78° C. in an acetone-dry ice bath was added n-BuLi (32 mL, 1.6 M in hexane, 51 mmol) dropwise. During the addition, the reaction temperature was kept below −60 degree. After completion of the addition, the reaction was stirred at −78° C. for 30 min. Then a solution of trimethyl borate (5.2 g, 51 mmol) in THF (12 ml) was added dropwise to the reaction mixture at −78° C. After completion of the addition, the reaction temperature was raised to 0° C. in 1 h and then quenched by 2N aqueous HCl (45 mL, 90 mmol). The organic layer was separated and the aqueous layer was extracted with 2×50 mL MTBE. The combined organic layers were washed once with brine and then dried over MgSO₄. The solvent was evaporated and the residue was dried under vacuum to give 13.5 g yellow solid. The solid was re-crystallized in iso-hexane and MTBE to give 8.1 g of (E)-(2-methyl-5-(4-methylpent-1-en-1-yl)phenyl)boronic acid as a white solid. ¹H NMR (CDCl₃): δ=8.23 (s, 1H, Ar—H), 7.43-7.05 (m, 2H, Ar—H), 6.42-6.15 (m, 2H), 2.80 (s, 3H, Ar—CH₃), 2.09 (dd, J=6.4 Hz, 6.4 Hz, 2 H), 1.79-1.66 (m, 1 H, (CH₃)₂CH—), 0.96 (d, J=6.4 Hz, 6 H, 2CH₃). ¹³C NMR (CDCl₃): δ=144.8 (s), 134.9 (d), 134.7 (s), 130.9 (d), 130.5 (d), 129.2 (d), 125.8 (d), 42.5 (t), 28.7 (d), 22.4 (q).

I) (E)-3-(2-Methyl-5-(4-methylpent-1-en-1-yl)phenyl)propanal

To a 250 mL round-bottomed flask was added [RhCl(cod)]₂ (0.0026 g, 0.0058 mmol), cycloocta-1,5-diene (0.062 g, 0.58 mmol), and potassium phosphate (2.45 g, 11.6 mmol) in dioxane (20 ml) and water (3.0 mL) to give a yellowish solution. (E)-(2-Methyl-5-(4-methylpent-1-en-1-yl)phenyl)boronic acid (2.52 g, 11.6 mmol) and acroleine (0.97 g, 17.3 mmol) were added. The reaction mixture was heated to 85° C. under argon atmosphere for 4 h. The mixture was cooled to room temperature and was diluted with water (15 mL). The reaction mixture was extracted with 2×50 mL MTBE. The combined organic layers were washed once with brine and then dried over MgSO₄. The solvent was evaporated and the crude product was purified by column chromatography (iso-hexane/MTBE=20:1) and Kugelrohr distillation to give 0.8 g of (E)-3-(2-methyl-5-(4-methylpent-1-en-1-yl)phenyl)propanal as a colorless liquid. ¹H NMR (CDCl₃): δ=9.95-9.82 (m, 1H, CHO), 7.20-7.04 (m, 3 H, Ar—H), 6.30 (d, J=15.8 Hz, 1 H, Ar—CH=CH—), 6.23-6.09 (m, 1 H, Ar—CH=CH—CH₂—), 2.91 (t, J=7.6 Hz, 2 H, Ar—CH₂—CH₂—CHO), 2.80-2.70 (m, 2H, Ar—CH₂—CH₂—CHO), 2.28 (s, 3 H, Ar—CH₃), 2.08 (dd, J=6.7 Hz, 2 H, (CH₃)₂CH—CH₂—CH=), 1.75-1.69 (m, 1 H, (CH₃)₂CH—), 0.93 (d, J=6.7 Hz, 6 H, 2CH₃). ¹³C NMR (CDCl₃): δ=201.6 (d), 138.5 (s), 136.0 (s), 134.4 (s), 130.6 (d), 130.5 (d), 129.2 (d), 126.3 (d), 123.9 (d), 44.1 (d), 42.4 (t), 28.6 (d), 25.5 (t), 22.4 (q), 19.0 (q). MS: m/z (%)=230 (22) [M⁺], 187 (3), 169 (5), 156 (5), 143 (100), 128 (21), 115 (8), 105 (1), 91 (4), 77 (3), 65 (2), 51 (1), 41 (3).

J) 3-(2-Methyl-5-(4-methylpentyl)phenyl)propanal

To a 100 mL round-bottomed flask was added (E)-3-(2-methyl-5-(4-methylpent-1-en-1-yl)phenyl)propanal (0.50 g, 2.2 mmol) in ethyl acetate (10 ml) to give a colorless solution. The solution was de-gased and purged with argon. Palladium on charcol (0.05 g, Pd content of 10%) was added. The reaction was stirred under hydrogen atmosphere for 2 h until completion of the conversion (confirmed by GC). The reaction mixture was filtered through a small pad of silica gel and the solid was rinsed with ethyl acetate. The filtrate was collected and concentrated. The residue obtained was distilled by Kugelrohr to give 0.45 g of 3-(2-methyl-5-(4-methylpentyl)phenyl)propanal as a colorless liquid. Odor description: green, anisic, aldehydic, fatty. ¹H NMR (CDCl₃): δ=9.86-9.83 (m, 1H, CHO), 7.06 (d, J=8.0 Hz, 1H, Ar—H), 6.95 (d, J=8.0 Hz, 1H, Ar—H), 6.94 (s, 1H, Ar—H), 2.92 (t, J=7.7 Hz, 2 H, Ar—CH₂—CH₂—CHO), 2.73 (t, J=7.8 Hz, 2 H, Ar—CH₂—CH₂—CHO), 2.52 (t, J=7.8 Hz, 2 H, Ar—CH₂—CH₂—CH₂), 2.27 (s, 3 H, Ar—CH₃), 1.63-1.52 (m, 3 H, (CH₃)₂CH—CH₂—CH₂), 1.26-1.16 (m, 2 H, Ar—CH₂—CH₂—CH₂—), 0.87 (d, J=6.6 Hz, 6 H, 2 CH₃). ¹³C NMR (CDCl₃): δ=201.8 (d), 140.9 (s), 138.2 (s), 132.9 (s), 130.3 (d), 128.7 (d), 126.4 (d), 44.2 (t), 38.7 (t), 35.8 (t), 29.5 (t), 27.9 (d), 25.5 (t), 22.6 (q), 18.9 (q). MS: m/z (%)=232 (50) [M⁺], 214 (64), 204 (4), 188 (14), 176 (23), 161 (42), 143 (57), 129 (32), 119 (100), 105 (75), 91 (40), 77 (7), 65 (5), 55 (7), 43 (18).

The following compounds were prepared according to the sequence described in Example 11.

Example 12

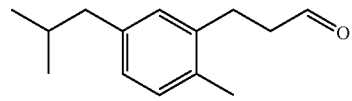

3-(5-Isobutyl-2-methylphenyl)propanal

Odor: aldehydic, floral, pungent

¹H NMR (CDCl₃): δ=9.86-9.83 (m, 1H, CHO), 7.05 (d, J=8.0 Hz, 1 H, Ar—H), 6.91 (d, J=8.0 Hz, 1 H, Ar—H), 6.90 (s, 1 H, Ar—H), 2.92 (t, J=7.6 Hz, 2 H, Ar—CH₂—CH₂—CHO), 2.73 (t, J=7.6 Hz, 2 H, Ar—CH₂—CH₂—CHO), 2.41 (d, 1=7.1 Hz, 2 H, Ar—CH₂—CH(CH₃)₂), 2.28 (s, 3 H, Ar—CH₃), 1.88-1.74 (m, 1H, (CH₃)₂CH—), 0.88 (d, J=6.6 Hz, 6 H, 2 CH₃). ¹³C NMR (CDCl₃): δ=201.8 (d), 139.6 (s), 137.9 (s), 132.9 (s), 130.1 (d), 129.4 (d), 127.2 (d), 45.0 (t), 44.2 (t), 30.2 (d), 25.5 (t), 22.4 (q), 18.8 (q). MS: m/z (%)=204 (37) [M⁺], 186 (32), 161 (83), 143 (62), 129 (17), 119 (100), 105 (36), 91 (32), 77 (11), 65 (5), 55 (4), 41 (9).

Example 13

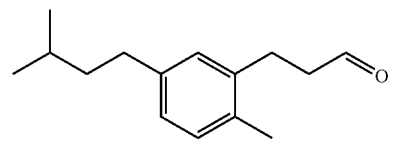 [SMILES: Cc1ccc(CCC(C)C)cc1CCC=O]

3-(5-Isopentyl-2-methyl phenyl)propanal

Odor: floral, aldehydic, watery, metallic

¹H NMR (CDCl₃): δ=9.86-9.82 (m, 1H, CHO), 7.05 (d, J=8.1 Hz, 1 H, Ar—H), 6.95 (d, J=8.1 Hz, 1 H, Ar—H), 6.94 (s, 1 H, Ar—H), 2.91 (t, J=7.6 Hz, 2 H, ArCH₂—CH₂—CHO), 2.73 (t, J=7.6 Hz, 2 H, Ar—CH₂—CH₂—CHO), 2.54 (t, J=8.0 Hz, 2 H, Ar—CH_z—CH₂—CH(CH₃)₂), 2.27 (s, 3

H, Ar—CH$_3$), 1.64-1.52 (m, 1H, (CH$_3$)$_2$CH—), 1.51-1.41 (m, 2 H, Ar—CH$_2$—CH$_2$—CH(CH$_3$)$_2$), 0.92 (d, J=6.4 Hz, 6 H, 2 CH$_3$). $^{13}$C NMR (CDCl$_3$): δ=201.8 (d), 141.0 (s), 138.2 (s), 132.9 (s), 130.3 (d), 128.7 (d), 126.4 (d), 44.2 (t), 41.0 (t), 33.4 (t), 27.7 (d), 25.1 (t), 22.6 (q), 18.9 (q). MS: m/z (%)=218 (44) [M$^+$], 200 (20), 175 (5), 161 (27), 144 (80), 131 (23), 118 (100), 105 (48), 91 (41), 77 (12), 65 (5), 55 (5), 41 (14).

Example 14

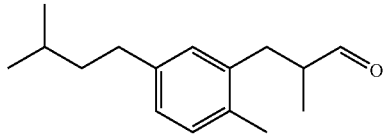 [SMILES: Cc1ccc(CCC(C)C)cc1CC(C)C=O]

3-(5-Isopentyl-2-methylphenyl)-2-methylpropanal

Odor: watery, aldehydic $^1$H NMR (CDCl$_3$): δ=9.75-9.69 (m, 1H, CHO), 7.06 (d, J=7.6 Hz, 1 H, Ar—H), 6.95 (d, J=8.0 Hz, 1 H, Ar—H), 6.92 (s, 1 H, Ar—H), 3.06 (dd, J=5.8 Hz, 13.6 Hz, 2 H, Ar—CH$_2$—CH(CH$_3$)—CHO), 2.69-2.58 (m, 1H, CH—CHO), 2.54 (t, J=7.4 Hz, 2 H, Ar—CH$_2$—CH$_2$—CH(CH$_3$)$_2$), 2.27 (s, 3 H, Ar—CH$_3$), 1.65-1.51 (m, 1H, (CH$_3$)$_2$CH—), 1.50-1.41 (m, 2 H, Ar—CH$_2$—CH$_2$—CH(CH$_3$)$_2$), 1.11 (d, J=6.9 Hz, 3 H, CH$_3$), 0.92 (d, J=6.4 Hz, 6 H, 2 CH$_3$). $^{13}$C NMR (CDCl$_3$): δ=204.5 (d), 140.7 (s), 136.9 (s), 133.1 (s), 130.4 (d), 129.8 (d), 126.5 (d), 46.9 (d), 41.0 (t), 33.9 (t), 33.3 (t), 27.7 (d), 22.6 (q), 19.1 (q), 13.5 (q). MS: m/z (%)=232 (25) [M$^+$], 214 (21), 199 (5), 175 (34), 158 (33), 143 (14), 131 (15), 119 (100), 105 (38), 91 (25), 77 (8), 65 (4), 55 (3), 41 (10).

Example 15

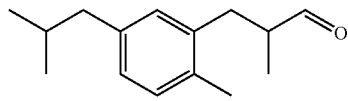 [SMILES: Cc1ccc(CC(C)C)cc1CC(C)C=O]

3-(5-Isobutyl-2-methylphenyl)-2-methylpropanal

Odor: green, fatty, aldehydic, bisabolene-like $^1$H NMR (CDCl$_3$): δ=9.73-9.70 (m, 1H, CHO), 7.06 (d, J=7.7 Hz, 1 H, Ar—H), 6.91 (d, J=7.7 Hz, 1 H, Ar—H), 6.88 (s, 1 H, Ar—H), 3.11-3.03 (m, 1 H, Ar—CH$_2$—CH(CH$_3$)—CHO), 2.70-2.49 (m, 2 H, Ar—CH$_2$—CH(CH$_3$)—CHO), 2.41 (d, J=7.1 Hz, 2H, Ar—CH$_2$—CH(CH$_3$)$_2$), 2.28 (s, 3 H, Ar—CH$_3$), 1.86-1.77 (m, 1H, (CH$_3$)$_2$CH—), 1.10 (d, J=6.6 Hz, 3 H, CH$_3$), 0.88 (d, J=6.6 Hz, 6 H, 2 CH$_3$). $^{13}$C NMR (CDCl$_3$): δ=204.6 (d), 139.3 (s), 136.6 (s), 133.2 (s), 130.6 (d), 130.3 (d), 127.3 (d), 46.9 (d), 45.0 (t), 33.9 (t), 30.3 (d), 22.4 (q), 22.3 (q), 19.0 (q), 13.4 (q). MS: m/z (%)=218 (35) [M$^+$], 200 (47), 185 (7), 175 (46), 161 (86), 147 (29), 129 (15), 119 (100), 105 (72), 91 (32), 77 (12), 67 (4), 57 (7), 41 (13).

Example 16

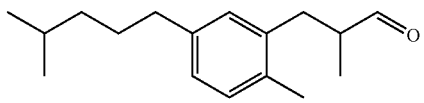 [SMILES: Cc1ccc(CCCC(C)C)cc1CC(C)C=O]

2-Methyl-3-(2-methyl-5-(4-methylpentyl)phenyl)propanal

Odor: watery, aldehydic, metallic, sharp, citrus, mandarin $^1$H NMR (CDCl$_3$): δ=9.73-9.70 (m, 1H, CHO), 7.06 (d, J=7.6 Hz, 1H, Ar—H), 6.95 (d, J=7.6 Hz, 1H, Ar—H), 6.92 (s, 1H, Ar—H), 3.11-3.03 (m, 1 H, Ar—CH$_2$—CH(CH$_3$)—CHO), 2.66-2.48 (m, 4 H), 2.27 (s, 3 H, Ar—CH$_3$), 1.63-1.48 (m, 3 H, (CH$_3$)$_2$CH—CH$_2$—CH$_2$), 1.25-1.16 (m, 2 H, Ar—CH$_2$—CH$_2$—CH$_2$—), 1.10 (d, J=6.9 Hz, 3 H, CH$_3$), 0.86 (d, J=6.6 Hz, 6 H, 2 CH$_3$). $^{13}$C NMR (CDCl$_3$): δ=204.4 (d), 140.6 (s), 136.9 (s), 133.2 (s), 130.4 (d), 129.9 (d), 126.6 (d), 46.9 (d), 38.7 (t), 35.8 (t), 33.9 (t), 29.5 (t), 27.9 (d), 22.6 (q), 19.1 (q), 13.4 (q). MS: m/z (%)=246 (38) [M$^+$], 228 (73), 213 (13), 203 (5), 189 (53), 176 (31), 157 (32), 147 (32), 131 (22), 119 (98), 105 (100), 91 (37), 77 (12), 65 (5), 55 (9), 43 (24).

Example 17

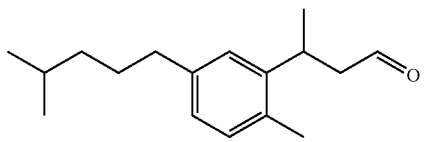 [SMILES: Cc1ccc(CCCC(C)C)cc1C(C)CC=O]

3-(2-Methyl-5-(4-methylpentyl)phenyl)butanal

Odor: weak, green, watery, floral $^1$H NMR (CDCl$_3$): δ=9.73-9.69 (m, 1H, CHO), 7.05 (d, J=7.7 Hz, 1H, Ar—H), 6.98 (s, 1H, Ar—H), 6.93 (d, J=7.7 Hz, 1H, Ar—H), 3.63-3.51 (m, 1 H, Ar—CH(CH$_3$)—CH$_2$—CHO), 2.79-2.60 (m, 2 H, CH—CH$_2$—CHO), 2.53 (t, J=7.8 Hz, 2 H, Ar—CH$_2$—), 2.32 (s, 3 H, Ar—CH$_3$), 1.63-1.49 (m, 3 H, (CH$_3$)$_2$CH—CH$_2$—CH$_2$—), 1.27 (d, J=6.9 Hz, 3 H, CH$_3$), 1.26-1.16 (m, 2 H, Ar—CH$_2$—CH$_2$—CH$_2$—), 0.87 (d, J=6.6 Hz, 6 H, 2 CH$_3$). $^{13}$C NMR (CDCl$_3$): δ=204.4 (d), 143.3 (s), 141.0 (s), 132.2 (s), 130.5 (d), 126.2 (d), 125.4 (d), 51.2 (d), 38.7 (t), 36.0 (t), 29.5 (t), 29.3 (d), 27.9 (d), 22.6 (q), 21.6 (q), 19.0 (q). MS: m/z (%)=246 (89) [M$^+$], 228 (42), 213 (14), 203 (100), 189 (14), 175 (31), 161 (34), 143 (26), 133 (90), 119 (55), 105 (78), 91 (35), 77 (11), 65 (5), 55 (9), 43 (31).

Example 18

In this floral perfume formulation 3-(4-isobutyl-2-methylphenyl)propanal increases the floral signature and makes this chypre fresher with a nice floral vibration, emphazising the softness of the woods while maintaining the fruity spicy tonality

| | | |
|---|---|---|
| ETHYL PHENYL ALCOHOL | 60-12-8 | 20.00 |
| ALD C 11 UNDECYLENIQUE at 10% in BB | | 9.00 |
| AMBERMAX 10%/TEC | | 3.00 |
| BENZYL BENZOATE | 120-51-4 | 93.00 |
| BERGAMOTE ESS ITALIE ORPUR | 8007-75-8 | 75.00 |
| CASHMERAN | 33704-61-9 | 9.00 |
| CHENE EXTRAIT CO2/ETHANOL | | 8.00 |
| CITRON ESS ITALIE SFUMATRICE ORPUR | 8008-56-8 | 45.00 |
| DIHYDRO ISOJASMONATE METHYLE | 37172-53-5 | 100.00 |
| GALBANUM ESS CONCENTREE 10% in DPG | | 25.00 |
| GERANIOL 980 | 106-24-1 | 15.00 |
| GIVESCONE | 57934-97-1 | 100.00 |
| GRAPEFRUIT ESS COSMOS | 8016-20-4 | 30.00 |
| JASMIN ABS COMMUNELLE | 8022-96-6 | 10.00 |
| JAVANOL | 198404-98-7 | 2.00 |
| KOHINOOL 862107-86-6 | | 20.00 |
| NONADIENOL-2,6 10%/TEC at 1% in BB | | 15.00 |
| OENANTHATE ALLYLE at 10% in BB | | 8.00 |
| PATCHOULI ESS FRACTION INDONESIE ORPUR | 8014-09-3 | 20.00 |
| PECHE PURE | 104-67-6 | 3.00 |
| PEPPERWOOD | 67643-70-3 | 55.00 |
| SYLKOLIDE | 676532-44-8 | 70.00 |
| VERTOFIX COEUR | 32388-55-9 | 120.00 |
| 3-(4-ISOBUTYL-2-METHYLPHENYL)PROPANAL | | 45.00 |
| | | 900.00 |

Example 19

In vitro metabolism study. A comparison of compounds of the present invention and Lilial™

Cryopreserved hepatocytes from male rats (Sprague Dawley; Lifetechnologies) were defrozen, washed in Cyropreserved Hepatocytes Recovery Medium (CHRM; Lifetechnologies) and suspended in Williams E Medium (WEM; Lifetechnologies). Lilial™, or the compounds of the present invention (final concentration: 100 µM) were added to the cells ($1 \times 10^6$ viable cells/ml) and suspensions were incubated up to 4 hours at 37° C. on a shaker in duplicate. Metabolism of testosterone was monitored as positive control. Decrease of the test compounds and formation of the corresponding benzoic acid derivative was determined by GC-MS analysis of methyl esters formed after derivatisation with trimethylsilyl diazomethane (Sigma-Aldrich) in methanol. The test compounds react with diazomethane yielding a methyl ketone which was used for the quantification of Lilial™ and the compound of formula (I). Metabolism was stopped with ice cold 1 M HCl, samples were extracted with tert-butyl methyl ether (MTBE) and analysed by GC-MS. Incubations containing testosterone as control were also stopped with ice cold 1 M HCl, centrifuged to separate the cells, filtrated and the decrease of testosterone analysed by LC-MS. To quantify decrease of the test substances and formation of benzoic acid metabolites, calibration curves of reference materials (Lilial™ and the compounds of the present invention, tert-butyl benzoic acid (Fluka) was prepared in hepatocyte incubation medium and analysed like the hepatocyte samples.

A rapid decrease of testosterone as positive control was observed indicating that the hepatocytes were metabolically active. The compounds of the present invention and Lilial™ were metabolised rapidly in rat hepatocytes and no residual compound except for 2% with one compound was measured after 4 h. Whereas tert-butyl benzoic acid was detected as metabolite of Lilial™ (3.4-3.9 µM) no benzoic acid derivatives were formed from compounds of the present invention (Table 1). Limit of detection was <1 µM.

Table 1 (below), shows the concentrations of Lilial™ and compounds of the present invention as well as corresponding benzoic acid metabolites in rat hepatocytes within 4 hours incubation. Initial test concentration at 0 hours incubation was 100 µM.

It is clear from the data presented in Table 1 that the ortho substituent at the benzene ring of the compounds of the present invention prevents the formation of the corresponding benzoic acid derivative in vitro. Since benzoic acid derivatives such as tert-butyl benzoic acid from Lilial™ cause reproductive toxicity in male rats, these toxic effects in male rats are prevented by the ortho-substituent of the compounds of the present invention.

| Test compound | Residual concentration (µM) | Benzoic acid derivative | Concentration (µM) |
|---|---|---|---|
| 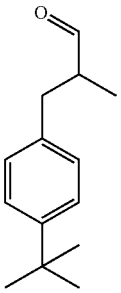 $C_{14}H_{20}O$ | 0 | 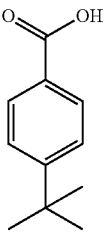 $C_{11}H_{14}O_2$ | 3.5-3.9 µM |
| 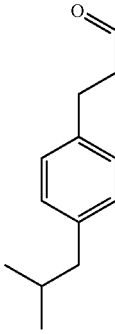 $C_{14}H_{20}O$ | 0 | 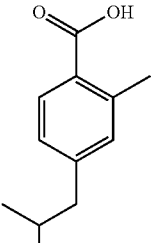 $C_{12}H_{16}O_2$ | not found |

-continued
| Test compound | Residual concentration (μM) | Benzoic acid derivative | Concentration (μM) |
|---|---|---|---|
| 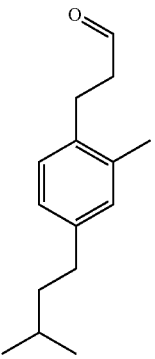 C$_{15}$H$_{22}$O | 0 | 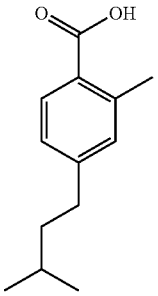 C$_{13}$H$_{18}$O$_2$ | not found |
| 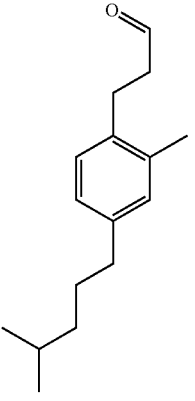 C$_{16}$H$_{24}$O | 0 | 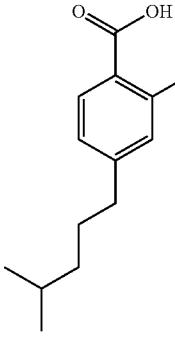 C$_{14}$H$_{20}$O$_2$ | not found |
| 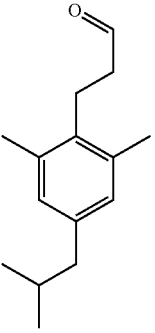 C$_{15}$H$_{22}$O | 0 | 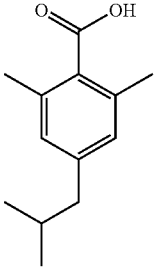 C$_{13}$H$_{18}$O$_2$ | not found |
| 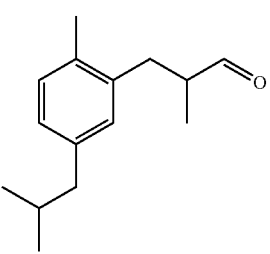 C$_{15}$H$_{22}$O | 0 | 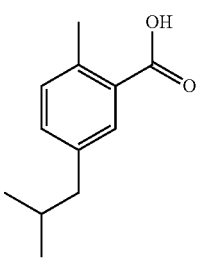 C$_{12}$H$_{16}$O$_2$ | not found |

| Test compound | Residual concentration (μM) | Benzoic acid derivative | Concentration (μM) |
|---|---|---|---|
| 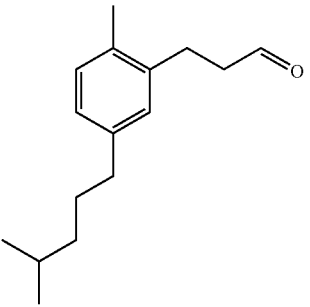 $C_{16}H_{24}O$ | 2.4 μM | 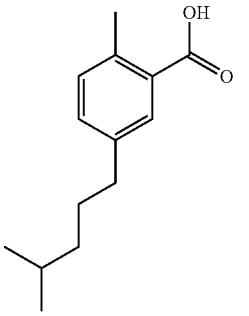 $C_{14}H_{20}O_2$ | not found |

The invention claimed is:

1. An aryl-substituted alkanal compound having a molecular weight of less than 300 g/mol and which bears a substituent on the aryl ring ortho to a substituent bearing the aldehyde functionality, represented by formula 3

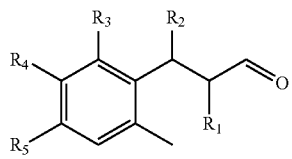

Formula 3 wherein $R_1$, $R_2$, and $R_3$ each independently represent H or methyl;

$R_4$ is H, or when $R_5$ is H, $R_4$ is an iso-butyl, sec-butyl or linear, saturated or unsaturated, unsubstituted or substituted, optionally with cyclopropyl groups, $C_5$-$C_7$ alkyl or alkenyl residue; and $R_5$ is H, or when $R_4$ is H, $R_5$ is an iso-butyl, sec-butyl or linear, saturated or unsaturated, unsubstituted or substitute, optionally with cyclopropyl groups, $C_5$-$C_7$ alkyl or alkenyl substituent;

or at least one compound selected from 5-isobutyl-2,3-dihydro-1H-indene-2-carbaldehyde and 3-(1,1,6-trimethyl-2,3-dihydro-1H-inden-5-yl)propanal;

and wherein said aryl-substituted alkanal compound is not 3-(5-(tert-butyl)-2-methylphenyl)propanal, 3-(5-(tert-butyl)-2-methylphenyl)-2-methylpropanal, 3-(5-isopropyl-2-methylphenyl)propanal, 3-(5-isopropyl-2-methylphenyl)-2-methylpropanal, 3-(5-ethyl-2-methylphenyl)propanal, 3-(5-ethyl-2-methylphenyl)-2-methylpropanal, 3-(4-(tert-butyl)-2-methylphenyl)propanal, 3-(4-(tert-butyl)-2-methylphenyl)-2-methylpropanal, 3-(4-isopropyl-2-methylphenyl)propanal, 3-(4-isopropyl-2-methylphenyl)-2-methylpropanal, 3-(4-ethyl-2-methylphenyl)propanal, 3-(4-ethyl-2-methylphenyl)-2-methylpropanal, or a compound of formula 3 wherein $R_1$ through $R_5$ is independently H or methyl.

2. The compound according to claim 1 represented by formula 4

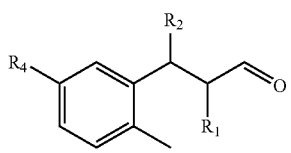

Formula 4 wherein $R_1$ and $R_2$, each independently may represent H or methyl; and $R_4$ represents an iso-butyl or sec-butyl group, or a saturated or unsaturated $C_5$-$C_7$ alkyl or alkenyl radical, which may be unsubstituted or substituted, optionally with cyclopropyl groups.

3. The compound according to claim 1 represented by formula 5

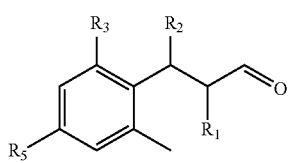

Formula 5 wherein $R_1$, $R_2$, and $R_3$ each independently may represent H or methyl; and $R_5$ is an iso-butyl or sec-butyl group, or a saturated or unsaturated $C_5$-$C_7$ alkyl or alkenyl residue, which may be unsubstituted or substituted, optionally with cyclopropyl groups.

4. The compound according to claim 1 represented by the formula

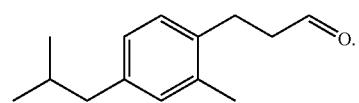

5. The compound according to claim 1 selected from the group consisting of 3-(4-isobutyl-2-methylphenyl)propanal, 3-(4-isobutyl-2,6-dimethylphenyl)propanal, 3-(4-isobutyl- 2-methylphenyl)-2-methylpropanal, 3-(4-isobutyl-2-methyl phenyl)butanal, 3-(4-(sec-butyl)-2-methylphenyl)propanal, 3-(2-methyl-4-(tert-pentyl)phenyl)propanal, 3-(4-isopentyl-2-methylphenyl)propanal, 3-(2-methyl-4-(4-methylpentyl) phenyl)propanal, 3-(2-methyl-5-(4-methylpentyl)phenyl) propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl)phenyl)propanal, 3-(5-isobutyl-2-methylphenyl)propanal, 3-(2-methyl-4-(2-methylbutyl)phenyl)propanal, 5-isobutyl-2,3-dihydro-1H-indene-2-carbaldehyde, and 3-(1,1,6-trimethyl-2,3-dihydro-1H-inden-5-yl)propanal.

6. A method of utilizing the compound according to claim 1 as a perfume ingredient exhibiting muguet odour characteristics to a personal care or household care composition comprising the step of adding to said composition the compound or a perfume composition containing said compound.

7. A perfume composition comprising the compound as defined in claim 1, which composition is free of any aryl-substituted alkanal, optionally free of any aryl-substituted propanal, odourants that are unsubstituted on the aryl ring at a position ortho to the substituent bearing the aldehyde functionality, and optionally free of 3-(4-tert-butylphenyl)-2-methylpropanal.

8. A personal care or household care composition perfumed with an aryl-substituted alkanal compound according to claim 1.

9. The personal care or household care composition according to claim 8 perfumed with a compound represented by formula 4

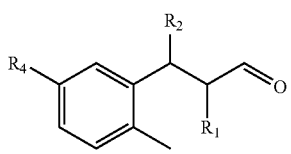

Formula 4 wherein
$R_1$ and $R_2$, each independently may represent H or methyl; and
$R_4$ represents an iso-butyl or sec-butyl group, or a saturated or unsaturated $C_5$-$C_7$ alkyl or alkenyl residue, which may be unsubstituted or substituted, optionally with cyclopropyl groups.

10. The personal care or household care composition according to claim 8 perfumed with a compound represented by formula 5

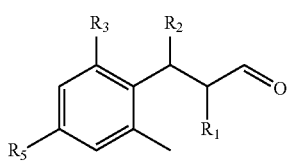

Formula 5 wherein
$R_1$, $R_2$, and $R_3$ each independently may represent H or methyl; and
$R_5$ is a an iso-butyl or sec-butyl group, or a saturated or unsaturated $C_5$-$C_7$ alkyl or alkenyl radical, which may be unsubstituted or substituted, optionally with cyclopropyl groups.

11. The personal care or household care composition according to claim 8 perfumed with a compound represented by the formula

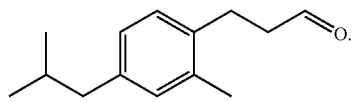

12. The personal care or household care composition according to claim 8 perfumed with a compound selected from the group consisting of 3-(4-isobutyl-2-methylphenyl) propanal, 3-(4-isobutyl-2,6-dimethylphenyl)propanal, 3-(4-isobutyl-2-methylphenyl)-2-methylpropanal, 3-(4-isobutyl-2-methylphenyl)butanal, 3-(4-(sec-butyl)-2-methylphenyl) propanal, 3-(2-methyl-4-(tert-pentyl)phenyl)propanal, 3-(4-isopentyl-2-methylphenyl)propanal, 3-(2-methyl-4-(4-methylpentyl)phenyl)propanal, 3-(2-methyl-5-(4-methylpentyl)phenyl)propanal, 3-(5-isopentyl-2-methylphenyl)propanal, 3-(5-isopentyl-2-methylphenyl)-2-methylpropanal, 3-(5-isobutyl-2-methylphenyl)-2-methylpropanal, 2-methyl-3-(2-methyl-5-(4-methylpentyl) phenyl)propanal, 3-(5-isobutyl-2-methylphenyl)propanal, 3-(2-methyl-4-(2-methylbutyl)phenyl)propanal, 5-isobutyl-2,3-dihydro-1H-indene-2-carbaldehyde, and 3 (1,1,6-trimethyl-2,3-dihydro-1H-inden-5-yl)propanal.

13. A personal care or household care composition according to claim 8 containing enzymes.

14. The personal or household care composition according to claim 13 characterised in that it is a textile treatment product.

15. The personal or household care composition according to claim 13 characterised in that it is a detergent composition.

16. A method of imparting muguet odour characteristics to a fine fragrance or consumer product comprising the step of adding thereto an aryl-substituted alkanal compound defined in claim 1, and selectively excluding from said fine fragrance or consumer product any aryl-substituted alkanal compounds, which are unsubstituted on the ring at the position ortho to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives, whereas said compounds being excluded on the basis that they do degrade to their benzoic acid derivatives.

* * * * *